(12) United States Patent
Burnett, Jr. et al.

(10) Patent No.: US 6,211,353 B1
(45) Date of Patent: *Apr. 3, 2001

(54) ISOLATED NUCLEIC ACID ENCODING A HUMAN MGLUR5

(75) Inventors: James Paul Burnett, Jr.; Nancy Gail Mayne; Robert Leon Sharp; Yvonne Marie Snyder, all of Indianapolis, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/660,148

(22) Filed: Jun. 7, 1996

Related U.S. Application Data

(62) Division of application No. 08/282,853, filed on Jul. 29, 1994.

(51) Int. Cl.⁷ .................................................. C12N 15/12
(52) U.S. Cl. ..................... 536/23.5; 435/69.1; 435/252.3; 435/320.1
(58) Field of Search .................................. 435/6, 7.1, 7.2, 435/69.1, 252.3, 320.1, 325; 530/350, 23.5

(56) References Cited

U.S. PATENT DOCUMENTS 5,521,297 * 5/1996 Daggett et al. ..................... 536/23.5

FOREIGN PATENT DOCUMENTS

WO 94/29449    12/1994    (WO) .............................. C12N/15/12

OTHER PUBLICATIONS

Takaaki Abe, et al., *The Journal of Biological Chemistry*, (1992), vol. 267, No. 19, pp. 13361–13368.

* cited by examiner

*Primary Examiner*—John Ulm
(74) *Attorney, Agent, or Firm*—Alexander Wilson

(57) ABSTRACT

This invention describes two novel human glutamate receptors, designated mGluR5A and mGluR5B. This invention also encompasses nucleic acids encoding this receptor, or a fragment thereof, as well as methods employing this receptor and the nucleic acid compounds.

29 Claims, 3 Drawing Sheets

ISOLATED NUCLEIC ACID ENCODING A HUMAN MGLUR5

This application is a division, of application Ser. No. 08/282,853 filed Jul. 29, 1994.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacological Science*, 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides an additional human excitatory amino acid receptor, designated mGluR5, to those previously known. The characterization and treatment of physiological disorders is hereby furthered.

SUMMARY OF THE INVENTION

This invention provides an isolated amino acid compound useful as a human metabotropic glutamate receptor, said compound comprising the amino acid sequence

```
Met Val Leu Leu Leu Ile Leu Ser Val Leu Leu Leu Lys Glu Asp Val
 1               5                  10                  15

Arg Gly Ser Ala Gln Ser Ser Glu Arg Arg Val Val Ala His Met Pro
                20                  25                  30

Gly Asp Ile Ile Ile Gly Ala Leu Phe Ser Val His His Gln Pro Thr
                35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
                100                 105                 110

Ile Arg Asp Ser Leu Ile Ser Ser Glu Glu Glu Glu Gly Leu Val Arg
            115                 120                 125

Cys Val Asp Gly Ser Ser Ser Ser Phe Arg Ser Lys Lys Pro Ile Val
        130                 135                 140

Gly Val Ile Gly Pro Gly Ser Ser Ser Val Ala Ile Gln Val Gln Asn
145                 150                 155                 160
```

-continued

```
Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
            195                 200                 205

Tyr Asn Trp Thr Tyr Val Ser Ala Val His Thr Glu Gly Asn Tyr Gly
            210                 215                 220

Glu Ser Gly Met Glu Ala Phe#Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Leu Thr Ser His Leu Pro Lys Ala Arg
            260                 265                 270

Val Val Ala Cys Phe Cys Glu Gly Met Thr Val Arg Gly Leu Leu Met
            275                 280                 285

Ala Met Arg Arg Leu Gly Leu Ala Gly Glu Phe Leu Leu Leu Gly Ser
            290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
                340                 345                 350

Pro Trp Phe Gln Glu Phe Trp Gln His Arg Phe Gln Cys Arg Leu Glu
            355                 360                 365

Gly Phe Pro Gln Glu Asn Ser Lys Tyr Asn Lys Thr Cys Asn Ser Ser
            370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
            420                 425                 430

Asp Gly Arg Lys Leu Leu Glu Ser Leu Met Lys Thr Asn Phe Thr Gly
            435                 440                 445

Val Ser Gly Asp Thr Ile Leu Phe Asp Glu Asn Gly Asp Ser Pro Gly
            450                 455                 460

Arg Tyr Glu Ile Met Asn Phe Lys Glu Met Gly Lys Asp Tyr Phe Asp
465                 470                 475                 480

Tyr Ile Asn Val Gly Ser Tr.p Asp Asn Gly Glu Leu Lys Met Asp Asp
                485                 490                 495

Asp Glu Val Trp Ser Lys Lys Ser Asn Ile Ile Arg Ser Val Cys Ser
            500                 505                 510

Glu Pro Cys Glu Lys Gly Gln Ile Lys Val Ile Arg Lys Gly Glu Val
            515                 520                 525

Ser Cys Cys Trp Thr Cys Thr Pro Cys Lys Glu Asn Glu Tyr Val Phe
            530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590
```

-continued

```
Ala Thr Leu Phe Val Thr Val Phe Ile Ile Tyr Arg Asp Thr Pro
            595                 600                 605

Val Val Lys Ser Ser Arg Glu Leu Cys Tyr Ile Ile Leu Ala Gly
        610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
            660                 665                 670

Leu Ala Gly Ser Lys Lys Ile Cys Thr Lys Lys Pro Arg Phe Met
        675                 680                 685

Ser Ala Cys Ala Gln Leu Val Ile Ala Phe Ile Leu Ile Cys Ile Gln
        690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
        755                 760                 765

Asn Glu Ala Lys Tyr Ile Ala Phe Thr Met Tyr Thr Thr Cys Ile Ile
770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
            805                 810                 815

Met Phe Val Pro Lys Val Tyr Ile Ile Leu Ala Lys Pro Glu Arg Asn
        820                 825                 830

Val Arg Ser Ala Phe Thr Thr Ser Thr Val Val Arg Met His Val Gly
        835                 840                 845

Asp Gly Lys Ser Ser Ser Ala Ala Ser Arg Ser Ser Ser Leu Val Asn
    850                 855                 860

Leu Trp Lys Arg Arg Gly Ser Ser Gly Glu Thr Leu Ser Ser Asn Gly
865                 870                 875                 880

Lys Ser Val Thr Trp Ala Gln Asn Glu Lys Ser Ser Arg Gly Gln His
                885                 890                 895

Leu Trp Gln Arg Leu Ser Ile His Ile Asn Lys Lys Glu Asn Pro Asn
            900                 905                 910

Gln Thr Ala Val Ile Lys Pro Phe Pro Lys Ser Thr Glu Ser Arg Gly
        915                 920                 925

Leu Gly Ala Gly Ala Gly Ala Gly Gly Ser Ala Gly Val Gly Ala
        930                 935                 940

Thr Gly Gly Ala Gly Cys Ala Gly Ala Gly Pro Gly Pro Glu Ser
945                 950                 955                 960

Pro Asp Ala Gly Pro Lys Ala Leu Tyr Asp Val Ala Glu Ala Glu Glu
                965                 970                 975

His Phe Pro Ala Pro Ala Arg Pro Arg Ser Pro Ser Pro Ile Ser Thr
            980                 985                 990

Leu Ser His Arg Ala Gly Ser Ala Ser Arg Thr Asp Asp Val Pro
        995                 1000                1005

Ser Leu His Ser Glu Pro Val Ala Arg Ser Ser Ser Ser Gln Gly Ser
```

-continued

```
           1010                1015                1020
Leu Met Glu Gln Ile Ser Ser Val Val Thr Arg Phe Thr Ala Asn Ile
1025                1030                1035                1040

Ser Glu Leu Asn Ser Met Met Leu Ser Thr Ala Ala Pro Ser Pro Gly
                1045                1050                1055

Val Gly Ala Pro Leu Cys Ser Ser Tyr Leu Ile Pro Lys Glu Ile Gln
            1060                1065                1070

Leu Pro Thr Thr Met Thr Thr Phe Ala Glu Ile Gln Pro Leu Pro Ala
        1075                1080                1085

Ile Glu Val Thr Gly Gly Ala Gln Pro Ala Ala Gly Ala Gln Ala Ala
    1090                1095                1100

Gly Asp Ala Ala Arg Glu Ser Pro Ala Ala Gly Pro Glu Ala Ala Ala
1105                1110                1115                1120

Ala Lys Pro Asp Leu Glu Glu Leu Val Ala Leu Thr Pro Pro Ser Pro
                1125                1130                1135

Phe Arg Asp Ser Val Asp Ser Gly Ser Thr Thr Pro Asn Ser Pro Val
            1140                1145                1150

Ser Glu Ser Ala Leu Cys Ile Pro Ser Ser Pro Lys Tyr Asp Thr Leu
        1155                1160                1165

Ile Ile Arg Asp Tyr Thr Gln Ser Ser Ser Pro Leu
    1170                1175                1180
``` hereinafter designated as SEQ ID NO:2.

The invention also provides an isolated nucleic acid compound that comprises a nucleic acid sequence which encodes for the amino acid compounds provided. Particularly this invention provides the isolated nucleic acid compound having the sequence

```
GTGATACAGA CCAGTGAGAA GGCAGCTTCT CCTTTTCACC TTCTTCTCCA TTCGCTACAT    60

GGGATTTTAT TGTTCAGAGT TTCTCAGGAC AAAGCTAGAG CTAATTTGTG TCTCTAATCC   120

TGGGCACTGG CCATTTGAAG CAGCCAAAGG TGCATTGACC AGGACTACGT GCAGCCCTTC   180

CTCCAGTGGG ACATAAGCAG GGGTTTTCTG TGGAAGTCTT AGTTGCATGA CATTCTACTG   240

TCAGCTGTGG AGTGTTCAGG TTTAGAAGAT CATGACCACA TGGATCATCT AACTAAATGG   300

TACATGGGGA CAAAATGGTC CTTTAGAAAA TACATCTGAA TTGCTGGCTA ATTTCTTGAT   360

TTGCGACTCA ACGTAGGACA TCGCTTGTTC GTAGCTATCA GAACCCTCCT GAATTCTCCC   420

CACCTTGCTA TCTTTATTGG CTTGAACTCC TTTCCTAAA ATG GTC CTT CTG TTG     474
                                            Met Val Leu Leu Leu
                                              1               5

ATC CTG TCA GTC TTA CTT TTG AAA. GAA GAT GTC CGT GGG AGT GCA CAG   522
Ile Leu Ser Val Leu Leu Leu Lys Glu Asp Val Arg Gly Ser Ala Gln
                10              15                  20

TCC AGT GAG AGG AGG GTG GTG GCT CAC ATG CCG GGT GAC ATC ATT ATT    570
Ser Ser Glu Arg Arg Val Val Ala His Met Pro Gly Asp Ile Ile Ile
            25                  30                  35

GGA GCT CTC TTT TCT GTT CAT CAC CAG CCT ACT GTG GAC AAA GTT CAT    618
Gly Ala Leu Phe Ser Val His His Gln Pro Thr Val Asp Lys Val His
            40                  45                  50

GAG AGG AAG TGT GGG GCG GTC CGT GAA CAG TAT GGC ATT CAG AGA GTG    666
Glu Arg Lys Cys Gly Ala Val Arg Glu Gln Tyr Gly Ile Gln Arg Val
        55                  60                  65

GAG GCC ATG CTG CAT ACC CTG GAA AGG ATC AAT TCA GAC CCC ACA CTC    714
```

-continued

```
                Glu Ala Met Leu His Thr Leu Glu Arg Ile Asn Ser Asp Pro Thr Leu
                 70                  75                  80                  85

TTG CCC AAC ATC ACA CTG GGC TGT GAG ATA AGG GAC TCC TGC TGG CAT          762
Leu Pro Asn Ile Thr Leu Gly Cys Glu Ile Arg Asp Ser Cys Trp His
                 90                  95                 100

TCG GCT GTG GCC CTA GAG CAG AGC ATT GAG TTC ATA AGA GAT CCC CTC          810
Ser Ala Val Ala Leu Glu Gln Ser Ile Glu Phe Ile Arg Asp Ser Leu
                105                 110                 115

ATT TCT TCA GAA GAG GAA GAA GGC TTG GTA CGC TGT GTG GAT GGC TCC          858
Ile Ser Ser Glu Glu Glu Glu Gly Leu Val Arg Cys Val Asp Gly Ser
                120                 125                 130

TCC TCT TCC TTC CGC TCC AAG AAG CCC ATA GTA GGG GTC ATT GGG CCT          906
Ser Ser Ser Phe Arg Ser Lys Lys Pro Ile Val Gly Val Ile Gly Pro
                135                 140                 145

GGC TCC AGT TCT GTA GCC ATT CAG GTC CAG AAT TTG CTC CAG CTT TTC          954
Gly Ser Ser Ser Val Ala Ile Gln Val Gln Asn Leu Leu Gln Leu Phe
150                 155                 160                 165

AAC ATA CCT CAG ATT GCT TAC TCA GCA ACC AGC ATG GAT CTG AGT GAC         1002
Asn Ile Pro Gln Ile Ala Tyr Ser Ala Thr Ser Met Asp Leu Ser Asp
                170                 175                 180

AAG ACT CTG TTC AAA TAT TTC ATG AGG GTT GTG CCT TCA GAT GCT CAG         1050
Lys Thr Leu Phe Lys Tyr Phe Met Arg Val Val Pro Ser Asp Ala Gln
                185                 190                 195

CAG GCA AGG GCC ATG GTG GAC ATA GTG AAG AGG TAC AAC TGG ACC TAT         1098
Gln Ala Arg Ala Met Val Asp Ile Val Lys Arg Tyr Asn Trp Thr Tyr
                200                 205                 210

GTA TCA GCC GTG CAC ACA GAA GGC AAC TAT GGA GAA AGT GGG ATG GAA         1146
Val Ser Ala Val His Thr Glu Gly Asn Tyr Gly Glu Ser Gly Met Glu
                215                 220                 225

GCC TTC AAA GAT ATG TCA GCG AAG GAA GGG ATT TGC ATC GCC CAC TCT         1194
Ala Phe Lys Asp Met Ser Ala Lys Glu Gly Ile Cys Ile Ala His Ser
230                 235                 240                 245

TAC AAA ATC TAC AGT AAT GCA GGG GAG CAG AGC TTT GAT AAG CTG CTG         1242
Tyr Lys Ile Tyr Ser Asn Ala Gly Glu Gln Ser Phe Asp Lys Leu Leu
                250                 255                 260

AAG AAG CTC ACA AGT CAC TTG CCC AAG GCC CGG GTG GTG GCC TGC TTC         1290
Lys Lys Leu Thr Ser His Leu Pro Lys Ala Arg Val Val Ala Cys Phe
                265                 270                 275

TGT GAG GGC ATG ACG GTG AGA GGT CTG CTG ATG GCC ATG AGG CGC CTG         1338
Cys Glu Gly Met Thr Val Arg Gly Leu Leu Met Ala Met Arg Arg Leu
                280                 285                 290

GGT CTA GCG GGA GAA TTT CTG CTT CTG GGC AGT GAT GGC TGG GCT GAC         1386
Gly Leu Ala Gly Glu Phe Leu Leu Leu Gly Ser Asp Gly Trp Ala Asp
                295                 300                 305

AGG TAT GAT GTG ACA GAT GGA TAT CAG CGA GAA GCT GTT GGT GGC ATC         1434
Arg Tyr Asp Val Thr Asp Gly Tyr Gln Arg Glu Ala Val Gly Gly Ile
310                 315                 320                 325

ACA ATC AAG CTC CAA TCT CCC GAT GTC AAG TGG TTT GAT GAT TAT TAT         1482
```

```
                         -continued
Thr Ile Lys Leu Gln Ser Pro Asp Val Lys Trp Phe Asp Tyr Tyr
            330                 335                 340

CTG AAG CTC CGG CCA GAA ACA AAC CAC CGA AAC CCT TGG TTT CAA GAA      1530

Leu Lys Leu Arg Pro Glu Thr Asn His Arg Asn Pro Trp Phe Gln Glu
            345                 350                 355

TTT TGG CAG CAT CGT TTT CAG TGC CGA CTG GAA GGG TTT CCA CAG GAG      1578

Phe Trp Gln His Arg Phe Gln Cys Arg Leu Glu Gly Phe Pro Gln Glu
            360                 365                 370

AAC AGC AAA TAC AAC AAG ACT TGC AAT AGT TCT CTG ACT CTG AAA ACA      1626

Asn Ser Lys Tyr Asn Lys Thr Cys Asn Ser Ser Leu Thr Leu Lys Thr
            375                 380                 385

CAT CAT GTT CAG GAT TCC AAA ATG GGA TTT GTG ATC AAC GCC ATC TAT      1674

His His Val Gln Asp Ser Lys Met Gly Phe Val Ile Asn Ala Ile Tyr
390                 395                 400                 405

TCG ATG GCC TAT GGG CTC CAC AAC ATG CAG ATG TCC CTC TGC CCA GGC      1722

Ser Met Ala Tyr Gly Leu His Asn Met Gln Met Ser Leu Cys Pro Gly
            410                 415                 420

TAT GCA GGA CTC TGT GAT GCC ATG AAG CCA ATT GAT GGA CGG AAA CTT      1770

Tyr Ala Gly Leu Cys Asp Ala Met Lys Pro Ile Asp Gly Arg Lys Leu
            425                 430                 435

TTG GAG TCC CTG ATG AAA ACC AAT TTT ACT GGG GTT TCT GGA GAT ACG      1818

Leu Glu Ser Leu Met Lys Thr Asn Phe Thr Gly Val Ser Gly Asp Thr
            440                 445                 450

ATC CTA TTC GAT GAG AAT GGA GAC TCT CCA GGA AGG TAT GAA ATA ATG      1866

Ile Leu Phe Asp Glu Asn Gly Asp Ser Pro Gly Arg Tyr Glu Ile Met
            455                 460                 465

AAT TTC AAG GAA ATG GGA AAA GAT TAC TTT GAT TAT ATC AAC GTT GGA      1914

Asn Phe Lys Glu Met Gly Lys Asp Tyr Phe Asp Tyr Ile Asn Val Gly
470                 475                 480                 485

AGT TGG GAC AAT GGA GAA TTA AAA ATG GAT GAT GAT GAA GTA TGG TCC      1962

Ser Trp Asp Asn Gly Glu Leu Lys Met Asp Asp Asp Glu Val Trp Ser
            490                 495                 500

AAG AAA AGC AAC ATC ATC AGA TCT GTG TGC AGT GAA CCA TGT GAG AAA      2010

Lys Lys Ser Asn Ile Ile Arg Ser Val Cys Ser Glu Pro Cys Glu Lys
            505                 510                 515

GGC CAG ATC AAG GTG ATC CGA AAG GGA GAA GTC AGC TGT TGT TGG ACC      2058

Gly Gln Ile Lys Val Ile Arg Lys Gly Glu Val Ser Cys Cys Trp Thr
            520                 525                 530

TGT ACA CCT TGT AAG GAG AAT GAG TAT GTC TTT GAT GAG TAC ACA TGC      2106

Cys Thr Pro Cys Lys Glu Asn Glu Tyr Val Phe Asp Glu Tyr Thr Cys
535                 540                 545

AAG GCA TGC CAA CTG GGG TCT TGG CCC ACT GAT GAT CTC ACA GGT TGT      2154

Lys Ala Cys Gln Leu Gly Ser Trp Pro Thr Asp Asp Leu Thr Gly Cys
550                 555                 560                 565

GAC TTG ATC CCA GTA CAG TAT CTT CGA TGG GGT G#AC CCT GAA CCC ATT      2202

Asp Leu Ile Pro Val Gln Tyr Leu Arg Trp Gly Asp Pro Glu Pro Ile
            570                 575                 580

GCA GCT GTG GTG TTT GCC TGC CTT GGC CTC CTG GCC ACC CTG TTT GTT      2250
```

```
                    -continued
Ala Ala Val Val Phe Ala Cys Leu Gly Leu Leu Ala Thr Leu Phe Val
            585                 590                 595
ACT GTA GTC TTC ATC ATT TAC CGT GAT ACA CCA GTA GTC AAG TCC TCA         2298
Thr Val Val Phe Ile Ile Tyr Arg Asp Thr Pro Val Val Lys Ser Ser
            600                 605                 610
AGC AGG GAA CTC TGC TAC ATT ATC CTT GCT GGC ATC TGC CTG GGC TAC         2346
Ser Arg Giu Leu Cys Tyr Ile Ile Leu Ala Giy Ile Cys Leu Gly Tyr
        615                 620                 625
TTA TGT ACC TTC TGC CTC ATT GCG AAG CCC AAA CAG ATT TAC TGC TAC         2394
Leu Cys Thr Phe Cys Leu Ile Ala Lys Pro Lys Gln Ile Tyr Cys Tyr
630                 635                 640                 645
CTT CAG AGA ATT GGC ATT GGT CTC TCC CCA GCC ATG AGC TAC TCA GCC         2442
Leu Gln Arg Ile Gly Ile Gly Leu Ser Pro Ala Met Ser Tyr Ser Ala
                650                 655                 660
CTT GTA ACA AAG ACC AAC CGT ATT GCA AGG ATC CTG GCT GGC AGC AAG         2490
Leu Val Thr Lys Thr Asn Arg Ile Ala Arg Ile Leu Ala Gly Ser Lys
            665                 670                 675
AAG AAG ATC TGT ACC AAA AAG CCC AGA TTC ATG AGT GCC TGT GCC CAG         2538
Lys Lys Ile Cys Thr Lys Lys Pro Arg Phe Met Ser Ala Cys Ala Gln
        680                 685                 690
CTA GTG ATT GCT TTC ATT CTC ATA TGC ATC CAG TTG GGC ATC ATC GTT         2586
Leu Val Ile Ala Phe Ile Leu Ile Cys Ile Gln Leu Gly Ile Ile Val
        695                 700                 705
GCC CTC TTT ATA ATG GAG CCT CCT GAC ATA ATG CAT GAC TAC CCA AGC         2634
Ala Leu Phe Ile Met Glu Pro Pro Asp Ile Met His Asp Tyr Pro Ser
710                 715                 720                 725
ATT CGA GAA GTC TAC CTG ATC TGT AAC ACC ACC AAC CTA GGA GTT GTC         2682
Ile Arg Glu Val Tyr Leu Ile Cys Asn Thr Thr Asn Leu Gly Val Val
                730                 735                 740
ACT CCA CTT GGA TAC AAT GGA TTG TTG ATT TTG AGC TGC ACC TTC TAT         2730
Thr Pro Leu Gly Tyr Asn Gly Leu Leu Ile Leu Ser Cys Thr Phe Tyr
            745                 750                 755
GCG TTC AAG ACC AGA AAT GTT CCA GCT AAC TTC AAC GAG GCC AAG TAT         2778
Ala Phe Lys Thr Arg Asn Val Pro Ala Asn Phe Asn Glu Ala Lys Tyr
        760                 765                 770
ATC GCC TTC ACA ATG TAC ACG ACC TGC ATT ATA TGG CTA GCT TTT GTG         2826
Ile Ala Phe Thr Met Tyr Thr Thr Cys Ile Ile Trp Leu Ala Phe Val
        775                 780                 785
CCA ATC TAC TTT GGC AGC AAC TAC AAA ATC ATC ACC ATG TGT TTC TCG         2874
Pro Ile Tyr Phe Gly Ser Ash Tyr Lys Ile Ile Thr Met Cys Phe Ser
790                 795                 800                 805
GTC AGC CTC AGT GCC ACA GTG GCC CTA GGC TGC ATG TTT GTG CCG AAG         2922
Val Ser Leu Ser Ala Thr Val Ala Leu Gly Cys Met Phe Val Pro Lys
                810                 815                 820
GTG TAC ATC ATC CTG GCC AAA CCA GAG AGA AAC GTG CGC AGC GCC TTC         2970
Val Tyr Ile Ile Leu Ala Lys Pro Glu Arg Asn Val Arg Ser Ala Phe
            825                 830                 835
ACC ACA TCT ACC GTG GTG CGC ATG CAT GTA GGG GAT GGC AAG TCA TCC         3018
```

```
                          -continued
Thr Thr Ser Thr Val Val Arg Met His Val Gly Asp Gly Lys Ser Ser
        840                 845                 850

TCC GCA GCC AGC AGA TCC AGC AGC CTA GTC AAC CTG TGG AAG AGA AGG      3066

Ser Ala Ala Ser Arg Ser Ser Ser Leu Val Asn Leu Trp Lys Arg Arg
    855                 860                 865

GGC TCC TCT GGG GAA ACC TTA AGT TCC AAT GGA AAA TCC GTC ACG TGG      3114

Gly Ser Ser Gly Glu Thr Leu Ser Ser Asn Gly Lys Ser Val Thr Trp
870                 875                 880                 885

GCC CAG AAT GAG AAG AGC AGC CGG GGG CAG CAC CTG TGG CAG CGC CTG      3162

Ala Gln Asn Glu Lys Ser Ser Arg Gly Gln His Leu Trp Gln Arg Leu
            890                 895                 900

TCC ATC CAC ATC AAC AAG AAA GAA AAC CCC AAC CAA ACG GCC GTC ATC      3210

Ser Ile His Ile Asn Lys Lys Glu Asn Pro Asn Gln Thr Ala Val Ile
                905                 910                 915

AAG CCC TTC CCC AAG AGC ACG GAG AGC CGT GGC CTG GGC GCT GGC GCT      3258

Lys Pro Phe Pro Lys Ser Thr Glu Ser Arg Gly Leu Gly Ala Gly Ala
                    920                 925                 930

GGC GCA GGC GGG AGC GCT GGG GGC GTG GGG GCC ACG GGC GGT GCG GGC      3306

Gly Ala Gly Gly Ser Ala Gly Gly Val Gly Ala Thr Gly Gly Ala Gly
    935                 940                 945

TGC GCA GGC GCC GGC CCA GGC GGG CCC GAG TCC CCA GAC GCC GGC CCC      3354

Cys Ala Gly Ala Gly Pro Gly Gly Pro Glu Ser Pro Asp Ala Gly Pro
950                 955                 960                 965

AAG GCG CTG TAT GAT GTG GCC GAG GCT GAG GAG CAC TTC CCG GCG CCC      3402

Lys Ala Leu Tyr Asp Val Ala Glu Ala Glu Glu His Phe Pro Ala Pro
                970                 975                 980

GCG CGG CCG CGC TCA CCG TCG CCC ATC AGC ACG CTG AGC CAC CGC GCG      3450

Ala Arg Pro Arg Ser Pro Ser Pro Ile Ser Thr Leu Ser His Arg Ala
            985                 990                 995

GGC TCG GCC AGC CGC ACG GAC GAC GAT GTG CCG TCG CTG CAC TCG GAG      3498

Gly Ser Ala Ser Arg Thr Asp Asp Asp Val Pro Ser Leu His Ser Glu
                1000                1005                1010

CCT GTG GCG CGC AGC AGC TCC TCG CAG GGC TCC CTC ATG GAG CAG ATC      3546

Pro Val Ala Arg Ser Ser Ser Ser Gln Gly Ser Leu Met Glu Gln Ile
    1015                1020                1025

AGC AGT GTG GTC ACC CGC TTC ACG GCC AAC ATC AGC GAG CTC AAC TCC      3594

Ser Ser Val Val Thr Arg Phe Thr Ala Asn Ile Ser Glu Leu Asn Ser
1030                1035                1040                1045

ATG ATG CTG TCC ACC GCG GCC CCC AGC CCC GGC GTC GGC GCC CCG CTC      3642

Met Met Leu Ser Thr Ala Ala Pro Ser Pro Gly Val Gly Ala Pro Leu
                1050                1055                1060

TGC TCG TCC TAC CTG ATC CCC AAA GAG ATC CAG TTG CCC ACG ACC ATG      3690

Cys Ser Ser Tyr Leu Ile Pro Lys Glu Ile Gln Leu Pro Thr Thr Met
            1065                1070                1075

ACG ACC TTT GCC GAA ATC CAG CCT CTG CCG GCC ATC GAA GTC ACG GGC      3738

Thr Thr Phe Ala Glu Ile Gln Pro Leu Pro Ala Ile Glu Val Thr Gly
                1080                1085                1090

GGC GCG CAG CCC GCG GCA GGG GCG CAG GCG GCT GGG GAC GCG GCC CGG      3786
```

```
Gly Ala Gln Pro Ala Ala Gly Ala Gln Ala Ala Gly Asp Ala Ala Arg
    1095                1100                1105

GAG AGC CCC GCG GCC GGT CCC GAG GCT GCG GCC GCC AAG CCA GAC CTG         3834

Glu Ser Pro Ala Ala Gly Pro Glu Ala Ala Ala Lys Pro Asp Leu
1110                1115                1120                1125

GAG GAG CTG GTG GCT CTC ACC CCG CCG TCC CCC TTC AGA GAC TCG GTG         3882

Glu Glu Leu Val Ala Leu Thr Pro Pro Ser Pro Phe Arg Asp Ser Val
                1130                1135                1140

GAC TCG GCG AGC ACA ACC CCC AAC TCG CCA GTG TCC GAG TCG GCC CTC         3930

Asp Ser Gly Ser Thr Thr Pro Asn Ser Pro Val Ser Glu Ser Ala Leu
                1145                1150                1155

TGT ATC CCG TCG TCT CCC AAA TAT GAC ACT CTT ATC ATA AGA GAT TAC         3978

Cys Ile Pro Ser Ser Pro Lys Tyr Asp Thr Leu Ile Ile Arg Asp Tyr
                1160                1165                1170

ACT CAG AGC TCC TCG CCGCTC TGAATGTCCC TGGAAAGCAC GCCGGCCTGC             4029

Thr Gln Ser Ser Ser Pro Leu
    1175                1180

GCGTGCGGAG CGGAGCCCCC CGTGTTCACA CACACACAAT GGCAAGCATA GCCGCCTCGT       4089

TACGGCCCAG GGGGAAGGTG CCAAGGGCAC CCCTTTATGG AAACACGAGA TCAGTAGCGC       4149

TATCTCATGA CAACCCACGA AGAAACCCAC GACAAATCTC GCGGCAGATT TTCTTCTA        4207
``` which is hereinafter designated as SEQ ID NO:1.

This invention further provides an isolated amino acid compound useful as a human metabotropic glutamate receptor, said compound comprising the amino acid sequence

```
Met Val Leu Leu Leu IleLeu Ser Val Leu Leu Leu Lys Glu Asp Val
 1                    5                 10                 15

Arg Gly Ser Ala Gln Ser Ser Glu Arg Arg Val Val Ala His Met Pro
                20                 25                 30

Gly Asp Ile Ile Ile Gly Ala Leu Phe Ser Val His His Gln Pro Thr
            35                 40                 45

Val Asp Lys Val His Glu Arg Lys Cys Gly Ala Val Arg Glu Gln Tyr
        50                 55                 60

Gly Ile Gln Arg Val Glu Ala Met Leu His Thr Leu Glu Arg Ile Asn
 65                 70                 75                 80

Ser Asp Pro Thr Leu Leu Pro Asn Ile Thr Leu Gly Cys *Glu Ile Arg
                85                 90                 95

Asp Ser Cys Trp His Ser Ala Val Ala Leu Glu Gln Ser Ile Glu Phe
                100                105                110

Ile Arg Asp Ser Leu Ile Ser Ser Glu Glu Glu Gly Leu Val Arg
            115                120                125

Cys Val Asp Gly Ser Ser Ser Phe Arg Ser Lys Lys Pro Ile Val
        130                135                140

Gly Val Ile Gly Pro Gly Ser Ser Val Ala Ile Gln Val Gln Asn
145                150                155                160

Leu Leu Gln Leu Phe Asn Ile Pro Gln Ile Ala Tyr Ser Ala Thr Ser
                165                170                175

Met Asp Leu Ser Asp Lys Thr Leu Phe Lys Tyr Phe Met Arg Val Val
                180                185                190

Pro Ser Asp Ala Gln Gln Ala Arg Ala Met Val Asp Ile Val Lys Arg
```

-continued

```
            195                 200                     205
Tyr Asn Trp Thr Tyr Val Ser Ala Val His Thr Glu Gly Asn Tyr Gly
    210                     215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
                260                 265             270

Val Val Ala Cys Phe Cys Glu Gly Met Thr Val Arg Gly Leu Leu Met
            275                 280                 285

Ala Met Arg Arg Leu Gly Leu Ala Gly Glu Phe Leu Leu Leu Gly Ser
        290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
                340                 345                 350

Pro Trp Phe Gln Glu Phe Trp Gln His Arg Phe Gln Cys Arg Leu Glu
                355                 360                 365

Gly Phe Pro Gln Glu Asn Ser Lys Tyr Asn Lys Thr Cys Asn Ser Ser
        370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
                420                 425                 430

Asp Gly Arg Lys Leu Leu Glu Ser Leu Met Lys Thr Asn Phe Thr Gly
            435                 440                 445

Val Ser Gly Asp Thr Ile Leu Phe Asp Glu Asn Gly Asp Ser Pro Gly
        450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
            500                 505                 510

Glu Pro Cys Glu Lys Gly Gln Ile Lys Val Ile Arg Lys Gly Glu Val
        515                 520                 525

Ser Cys Cys Trp Thr Cys Thr Pro Cys Lys Glu Asn Glu Tyr Val Phe
        530                 535                 540

Asp Glu Tyr Thr Cys Lys Ala Cys Gln Leu Gly Ser Trp Pro Thr Asp
545                 550                 555                 560

Asp Leu Thr Gly Cys Asp leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Val Phe Ile Ile Tyr Arg Asp Thr Pro
        595                 600                 605

Val Val Lys Ser Ser Ser Arg Glu Leu Cys Tyr Ile Ile Leu Ala Gly
        610                 615                 620
```

```
Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
            660                 665                 670

Leu Ala Gly Ser Lys Lys Lys Ile Cys Thr Lys Lys Pro Arg Phe Met
        675                 680                 685

Ser Ala Cys Ala Gln Leu Val Ile Ala Phe Ile Leu Ile Cys Ile Gln
    690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
        755                 760                 765

Asn Glu Ala Lys Tyr Ile Ala Phe Thr Met Tyr Thr Thr Cys Ile Ile
    770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Lys Val Tyr Ile Ile Leu Ala Lys Pro Glu Arg Asn
            820                 825                 830

Val Arg Ser Ala Phe Thr Thr Ser Thr Val Val Arg Met His Val Gly
        835                 840                 845

Asp Gly Lys Ser Ser Ala Ala Ser Arg Ser Ser Ser Leu Val
    850                 855                 860

Leu Trp Lys Arg Arg Gly Ser Ser Gly Glu Thr Leu Arg Tyr Lys Asp
865                 870                 875                 880

Arg Arg Leu Ala Gln His Lys Ser Glu Ile Glu Cys Phe Thr Pro Lys
                885                 890                 895

Gly Ser Met Gly Asn Gly Gly Arg Ala Thr Met Ser Ser Ser Asn Gly
            900                 905                 910

Lys Ser Val Thr Trp Ala Gln Asn Glu Lys Ser Ser Arg Gly Gln His
        915                 920                 925

Leu Trp Gln Arg Leu Ser Ile His Ile Asn Lys Lys Glu Asn Pro Asn
930                 935                 940

Gln Thr Ala Val Ile Lys Pro Phe Pro Lys Ser Thr Glu Ser Arg Gly
945                 950                 955                 960

Leu Gly Ala Gly Ala Gly Gly Ser Ala Gly Val Gly Ala
                965                 970                 975

Thr Gly Gly Ala Gly Cys Ala Gly Ala Gly Pro Gly Gly Pro Glu Ser
            980                 985                 990

Pro Asp Ala Gly Pro Lys Ala Leu Tyr Asp Val Ala Glu Ala Glu Glu
        995                 1000                1005

His Phe Pro Ala Pro Ala Arg Pro Arg Ser Pro Ser Pro Ile Ser Thr
    1010                1015                1020

Leu Ser His Arg Ala Gly Ser Ala Ser Arg Thr Asp Asp Val Pro
1025                1030                1035                1040

Ser Leu His Ser Glu Pro Val Ala Arg Ser Ser Ser Set Gln Gly Ser
                1045                1050                1055
```

```
Leu Met Glu Gln Ile Ser Ser Val Val Thr Arg Phe Thr Ala Asn Ile
            1060                1065                1070

Ser Glu Leu Asn Ser Met Met Leu Ser Thr Ala Ala Pro Ser Pro Gly
        1075                1080                1085

Val Gly Ala Pro Leu Cys Ser Ser Tyr Leu Ile Pro Lys Glu Ile Gln
    1090                1095                1100

Leu Pro Thr Thr Met Thr Thr Phe Ala Glu Ile Gln Pro Leu Pro Ala
1105                1110                1115                1120

Ile Glu Val Thr Gly Gly Ala Gln Pro Ala Ala Gly Ala Gln Ala Ala
                1125                1130                1135

Gly Asp Ala Ala Arg Glu Ser Pro Ala Ala Gly Pro Glu Ala Ala Ala
                1140                1145                1150

Ala Lys Pro Asp Leu Glu Glu Leu Val Ala Leu Thr Pro Pro Ser Pro
        1155                1160                1165

Phe Arg Asp Ser Val Asp Ser Gly Ser Thr Thr Pro Asn Ser Pro Val
        1170                1175                1180

Ser Glu Ser Ala Leu Cys Ile Pro Ser Ser Pro Lys Tyr Asp Thr Leu
1185                1190                1195                1200

Ile Ile Arg Asp Tyr Thr Gln Ser Ser Ser Pro Leu
                1205                1210
``` hereinafter designated as SEQ ID NO:5.

The invention also provides an isolated nucleic acid compound that comprises a nucleic acid sequence which encodes for the amino acid compounds provided. Particularly this invention provides the isolated nucleic acid compound having the sequence

```
GTGATACAGA CCAGTGAGAA GGCAGCTTCT CCTTTTCACC TTCTTCTCCA TTCGCTACAT    60

GGGATTTTAT TGTTCAGAGT TTCTCAGGAC AAAGCTAGAG CTAATTTGTG TCTCTAATCC   120

TGGGCACTGG CCATTTGAAG CAGCCAAAGG TGCATTGACC AGGACTACGT GCAGCCCTTC   180

CTCCAGTGGG ACATAAGCAG GGGTTTTCTG TGGAAGTCTT AGTTGCATGA CATTCTACTG   240

TCAGCTGTGG AGTGTTCAGG TTTAGAAGAT CATGACCACA TGGATCATCT AACTAAATGG   300

TACATGGGGA CAAAATGGTC CTTTAGAAAA TACATCTGAA TTGCTGGCTA ATTTCTTGAT   360

TTGCGACTCA ACGTAGGACA TCGCTTGTTC GTAGCTATCA GAACCCTCCT GAATTCTCCC   420

CACCTTGCTA TCTTTATTGG CTTGAACTCC TTTCCTAAA  ATG GTC CTT CTG TTG    474
                                            Met Val Leu Leu Leu
                                              1               5

ATC CTG TCA GTC TTA CTT TTG AAA GAA GAT GTC CGT GGG AGT GCA CAG    522
Ile Leu Ser Val Leu Leu Leu Lys Glu Asp Val Arg Gly Ser Ala Gln
            10                  15                  20

TCC AGT GAG AGG AGG GTG GTG GCT CAC ATG CCG GGT GAC ATC ATT ATT    570
Ser Ser Glu Arg Arg Val Val Ala His Met Pro Gly Asp Ile Ile Ile
        25                  30                  35

GGA GCT CTC TTT TCT GTT CAT CAC CAG CCT ACT GTG GAC AAA GTT CAT    618
Gly Ala Leu Phe Ser Val His His Gln Pro Thr Val Asp Lys Val His
            40                  45                  50

GAG AGG AAG TGT GGG GCG GTC CGT GAA CAG TAT GGC ATT CAG AGA GTG    666
Glu Arg Lys Cys Gly Ala Val Arg Glu Gln Tyr Gly Ile Gln Arg Val
        55                  60                  65

GAG GCC ATG CTGCAT ACC CTG GAA AGG ATC AAT TCA GAC CCC ACA CTC     714
```

-continued

```
Glu Ala Met Leu His Thr Leu Glu Arg Ile Asn Ser Asp Pro Thr Leu
70              75                  80                  85
TTG CCC AAC ATC ACA CTG GGC TGT GAG ATA AGG GAC TCC TGC TGG CAT        762
Leu Pro Asn Ile Thr Leu Gly Cys Glu Ile Arg Asp Ser Cys Trp His
                90                  95                  100
TCG GCT GTG GCC CTA GAG CAG AGC ATT GAG TTC ATA AGA GAT TCC CTC        810
Ser Ala Val Ala Leu Glu Gln Ser Ile Glu Phe Ile Arg Asp Ser Leu
                105                 110                 115
ATT TCT TCA GAA GAG GAA GAA GGC TTG GTA CGC TGT GTG GAT GGC TCC        858
Ile Ser Ser Glu Glu Glu Glu Gly Leu Val Arg Cys Val Asp Gly Ser
            120                 125                 130
TCC TCT TCC TTC CGC TCC AAG AAG CCC ATA GTA GGG GTC ATT GGG CCT        906
Ser Ser Ser Phe Arg Ser Lys Lys Pro Ile Val Gly Val Ile Gly Pro
        135                 140                 145
GGC TCC AGT TCT GTA GCC ATT CAC GTC CAG AAT TTG CTC CAG CTT TTC        954
Gly Ser Ser Ser Val Ala Ile His Val Gin Asn Leu Leu Gln Leu Phe
150                 155                 160                 165
AAC ATA CCT CAG ATT GCT TAC TCA GCA ACC AGC ATG GAT CTG AGT GAC       1002
Asn Ile Pro Gln Ile Ala Tyr Ser Ala Thr Ser Met Asp Leu Ser Asp
                170                 175                 180
AAG ACT CTG TTC AAA TAT TTC ATG AGG GTT GTG CCT TCA GAT GCT CAG       1050
Lys Thr Leu Phe Lys Tyr Phe Met Arg Val Val Pro Ser Asp Ala Gln
                185                 190                 195
CAG GCA AGG GCC ATG GTG GAC ATA GTG AAG AGG TAC AAC TGG ACC TAT       1098
Gln Ala Arg Ala Met Val Asp Ile Val Lys Arg Tyr Asn Trp Thr Tyr
                200                 205                 210
GTA TCA GCC GTG CAC ACA GAA GGC AAC TAT GGA GAA AGT GGG ATG GAA       1146
Val Ser Ala Val His Thr Glu Gly Asn Tyr Gly Glu Ser Gly Met Glu
                215                 220                 225
GCC TTC AAA GAT ATG TCA GCG AAG GAA GGG ATT TGC ATC GCC CAC TCT       1194
Ala Phe Lys Asp Met Ser Ala Lys Glu Gly Ile Cys Ile Ala His Ser
230                 235                 240                 245
TAC AAA ATC TAC AGT AAT GCA GGG GAG CAG AGC TTT GAT AAG CTG CTG       1242
Tyr Lys Ile Tyr Ser Asn Ala Gly Glu Gln Ser Phe Asp Lys Leu Leu
                250                 255                 260
AAG AAG CTC ACA AGT CAC TTG CCC AAG GCC CGG GTG GTG GCC TGC TTC       1290
Lys Lys Leu Thr Ser His Leu Pro Lys Ala Arg Val Val Ala Cys Phe
                265                 270                 275
TGT GAG GGC ATG ACG GTG AGA GGT CTG CTG ATG GCC ATG AGG CGC CTG       1338
Cys Glu Gly Met Thr Val Arg Gly Leu Leu Met Ala Met Arg Arg Leu
                280                 285                 290
GGT CTA GCG GGA GAA TTT CTG CTT CTG GGC AGT GAT GGC TGG GCT GAC       1386
Gly Leu Ala Gly Glu Phe Leu Leu Leu Gly Ser Asp Gly Trp Ala Asp
                295                 300                 305
AGG TAT GAT GTG ACA GAT GGA TAT CAG CGA GAA GCT GTT GGT GGC ATC       1434
Arg Tyr Asp Val Thr Asp Gly Tyr Gln Arg Glu Ala Val Gly Gly Ile
310                 315                 320                 325
ACA ATC AAG CTC CAA TCT CCC GAT GTC AAG TGG TTT GAT GAT TAT TAT       1482
```

```
                    Thr Ile Lys Leu Gln Ser Pro Asp Val Lys Trp Phe Asp Asp Tyr Tyr
                                    330                 335                 340

CTG AAG CTC CGG CCA GAA ACA AAC CAC CGA AAC CCT TGG TTT CAA GAA            1530
Leu Lys Leu Arg Pro Glu Thr Asn His Arg Asn Pro Trp Phe Gln Glu
            345                 350                 355

TTT TGG CAG CAT CGT TTT CAG T9C CGA CTG GAA GGG TTT CCA CAG GAG            1578
Phe Trp Gln His Arg Phe Gln Cys Arg Leu Glu Gly Phe Pro Gln Glu
                360                 365                 370

AAC AGC AAA TAC AAC AAG ACT TGC AAT AGT TCT CTG ACT CTG AAA ACA            1626
Asn Ser Lys Tyr Asn Lys Thr Cys Asn Ser Ser Leu Thr Leu Lys Thr
            375                 380                 385

CAT CAT GTT CAG GAT TCC AAA ATG GGA TTT GTG ATC AAC GCC ATC TAT            1674
His His Val Gln Asp Ser Lys Met Gly Phe Val Ile Asn Ala Ile Tyr
390                 395                 400                 405

TCG ATG GCC TAT GGG CTC CAC AAC ATG CAG ATG TCC CTC TGC CCA GGC            1722
Ser Met Aia Tyr Gly Leu His Asn Met Gln Met Ser Leu Cys Pro Gly
                410                 415                 420

TAT GCA GGA CTC TGT GAT GCC ATG AAG CCA ATT GAT GGA CGG AAA CTT            1770
Tyr Ala Gly Leu Cys Asp Ala Met Lys Pro Ile Asp Gly Arg Lys Leu
            425                 430                 435

TTG GAG TCC CTG ATG AAA ACC AAT TTT ACT GGG GTT TCT GGA GAT ACG            1818
Leu Glu Ser Leu Met Lys Thr Asn Phe Thr Gly Val Ser Gly Asp Thr
                440                 445                 450

ATC CTA TTC GAT GAG AAT GGA GAC TCT CCA GGA AGG TAT GAA ATA ATG            1866
Ile Leu Phe Asp Glu Asn Gly Asp Ser Pro Gly Arg Tyr Glu Ile Met
            455                 460                 465

AAT TTC AAG GAA ATG GGA AAA GAT TAC TTT GAT TAT ATC AAC GTT GGA            1914
Asn Phe Lys Glu Met Gly Lys Asp Tyr Phe Asp Tyr Ile Asn Val Gly
470                 475                 480                 485

AGT TGG GAC AAT GGA GAA TTA AAA ATG GAT GAT GAT GAA GTA TGG TCC            1962
Ser Trp Asp Asn Gly Glu Leu Lys Met Asp Asp Asp Glu Val Trp Ser
                490                 495                 500

AAG AAA AGC AAC ATC ATC AGA TCT GTG TGC AGT GAA CCA TGT GAG AAA            2010
Lys Lys Ser Asn Ile Ile Arg Ser Val Cys Ser Glu Pro Cys Glu Lys
            505                 510                 515

GGC CAG ATC AAG GTG ATC CGA AAG GGA GAA GTC AGC TGT TGT TGG ACC            2058
Gly Gln Ile Lys Val Ile Arg Lys Gly Glu Val Ser Cys Cys Trp Thr
                520                 525                 530

TGT ACA CCT TGT AAG GAG AAT GAG TAT GTC TTT GAT GAG TAC ACA TGC            2106
Cys Thr Pro Cys Lys Glu Asn Glu Tyr Val Phe Asp Glu Tyr Thr Cys
535                 540                 545

AAG GCA TGC CAA CTG GGG TCT TGG CCC ACT GAT GAT CTC ACA GGT TGT            2154
Lys Ala Cys Gln Leu Gly Ser Trp Pro Thr Asp Asp Leu Thr Gly Cys
550                 555                 560                 565

GAC TTG ATC CCA GTA CAG TAT CTT CGA TGG GGT GAC CCT GAA CCC ATT            2202
Asp Leu Ile Pro Val Gln Tyr Leu Arg Trp Gly Asp Pro Glu Pro Ile
            570                 575                 580

GCA GCT GTG GTG TTT GCC TGC CTT GGC CTC CTG GCC ACC TGT TTT GTT            2250
```

```
                Ala Ala Val Val Phe Ala Cys Leu Gly Leu Leu Ala Thr Leu Phe Val
                            585                 590                 595

ACT GTA GTC TTC ATC ATT TAC CGT GAT ACA CCA GTA GTC AAG TCC TCA              2298

Thr Val Val Phe Ile Ile Tyr Arg Asp Thr Pro Val Val Lys Ser Ser
            600                 605                 610

AGC AGG GAA CTC TGC TAC ATT ATC. CTT GCT GGC ATC TGC CTG GGC TAC             2346

Ser Arg Glu Leu Cys Tyr Ile Ile Leu Ala Gly Ile Cys Leu Gly Tyr
        615                 620                 625

TTA TGT ACC TTC TGC CTC ATT GCG AAG CCC AAA CAG ATT TAC TGC TAC              2394

Leu Cys Thr Phe Cys Leu Ile Ala Lys Pro Lys Gln Ile Tyr Cys Tyr
630                 635                 640                 645

CTT CAG AGA ATT GGC ATT GGT CTC TCC CCA GCC ATG AGC TAC TCA GCC              2442

Leu Gln Arg Ile Gly Ile Gly Leu Ser Pro Ala Met Ser Tyr Ser Ala
                650                 655                 660

CTT GTA ACA AAG ACC AAC CGT#ATT GCA AGG ATC CTG GCT GGC AGC AAG              2490

Leu Val Thr Lys Thr Asn Arg Ile Ala Arg Ile Leu Ala Gly Ser Lys
            665                 670                 675

AAG AAG ATC TGT ACC AAA AAG CCC AGA TTC ATG AGT GCC TGT GCC CAG              2538

Lys Lys Ile Cys Thr Lys Lys Pro Arg Phe Met Ser Ala Cys Ala Gln
        680                 685                 690

CTA GTG ATT GCT TTC ATT CTC ATA TGC ATC CAG TTG GGC ATC ATC GTT              2586

Leu Val Ile Ala Phe Ile Leu Ile Cys Ile Gln Leu Gly Ile Ile Val
695                 700                 705

GCC CTC TTT ATA ATG GAG CCT CCT GAC ATA ATG CAT GAC TAC CCA AGC              2634

Ala Leu Phe Ile Met Glu Pro Pro Asp Ile Met His Asp Tyr Pro Ser
710                 715                 720                 725

ATT CGA GAA GTC TAC CTG ATC TGT AAC ACC ACC AAC CTA GGA GTT GTC              2682

Ile Arg Glu Val Tyr Leu Ile Cys Asn Thr Thr Asn Leu Gly Val Val
                730                 735                 740

ACT CCA CTT GGA TAC AAT GGA TTG TTG ATT TTG AGC TGC ACC TTC TAT              2730

Thr Pro Leu Gly Tyr Asn Gly Leu Leu Ile Leu Ser Cys Thr Phe Tyr
            745                 750                 755

GCG TTC AAG ACC AGA AAT GTT CCA GCT AAC TTC AAC GAG GCC AAG TAT              2778

Ala Phe Lys Thr Arg Asn Val Pro Ala Asn Phe Asn Glu Ala Lys Tyr
        760                 765                 770

ATC GCC TTC ACA ATG TAC ACG ACC TGC ATT ATA TGG CTA GCT TTT GTG              2826

Ile Ala Phe Thr Met Tyr Thr Thr Cys Ile Ile Trp Leu Ala Phe Val
775                 780                 785

CCA ATC TAC TTT GGC AGC AAC TAC AAA ATC ATC ACC ATG TGT TTC TCG              2874

Pro Ile Tyr Phe Gly Ser Asn Tyr Lys Ile Ile Thr Met Cys Phe Ser
790                 795                 800                 805

GTC AGC CTC AGT GCC ACA GTG GCC CTA GGC TGC ATG TTT GTG CCG AAG              2922

Val Ser Leu Ser Ala Thr Val Ala Leu Gly Cys Met Phe Val Pro Lys
                810                 815                 820

GTG TAC ATC ATC CTG GCC AAA CCA GAG AGA AAC GTG CGC AGC GCC TTC              2970

Val Tyr Ile Ile Leu Ala Lys Pro Glu Arg Asn Val Arg Ser Ala Phe
            825                 830                 835

ACC ACA TCT ACC GTG GTG CGC ATG CAT GTA GGG GAT GGC AAG TCA TCC              3018
```

```
            Thr Thr Ser Thr Val Val Arg Met His Val Gly Asp Gly Lys Ser Ser
                    840                 845                 850

TCC GCA GCC AGC AGA TCC AGC AGC CTA GTC AAC CTG TGG AAG AGA AGG        3066

Ser Ala Ala Ser Arg Ser Ser Leu Val Asn Leu Trp Lys Arg Arg
        855                 860                 865

GGC TCC TCT GCG AAA ACC TTA AGG TAC AAA GAC AGG AGA CTG GCC CAG        3114

Gly Ser Ser Gly Glu Thr Leu Arg Tyr Lys Asp Arg Arg Leu Ala Gln
870                 875                 880                 885

CAC AAG TCG GAA ATA GAG TGT TTC ACC CCC AAA GGG AGT ATG GGG AAT        3162

His Lys Ser Glu Ile Glu Cys Phe Thr Pro Lys Gly Ser Met Gly Asn
                890                 895                 900

GGT GGG AGA GCA ACA ATG AGC AGT CCA AAT GGA AAA TCC GTC ACG TGG        3210

Gly Gly Arg Ala Thr Met Ser Ser Asn Gly Lys Ser Val Thr Trp
        905                 910                 915

GCC CAG AAT GAG AAGAGC AGCCGG GGG CAG CAC CTG TGG CAG CGC CTG          3258

Ala Gln Asn Glu Lys Ser Ser Arg Gly Gln His Leu Trp Gln Arg Leu
                920                 925                 930

TCC ATC CAC ATC AAC AAG AAA GAA AAC CCC AAC CAA ACG GCC GTC ATC        3306

Ser Ile His Ile Asn Lys Lys Glu Asn Pro Asn Gln Thr Aia Val Ile
        935                 940                 945

AAG CCC TTC CCC AAG AGC ACG GAG AGC CGT GGC CTG GGC GCT GGC GCT        3354

Lys Pro Phe Pro Lys Ser Thr Glu Ser Arg Gly Leu Gly Ala Gly Ala
950                 955                 960                 965

GGC GCA GGC GGG AGC GCT GGG GGC GTG GGG GCC ACG GGC GGT GCG GGC        3402

Gly Ala Gly Gly Ser Ala Gly Gly Val Gly Ala Thr Gly Gly Ala Gly
                970                 975                 980

TGC GCA GGC GCC GGC CCA GGC GGG CCC GAG TCC CCA GAC GCC GGC CCC        3450

Cys Ala Gly Ala Gly Pro Gly Gly Pro Glu Ser Pro Asp Ala Gly Pro
        985                 990                 995

AAG GCG CTG TAT GAT GTC GCC GAG GCT GAG GAG CAC TTC CCG GCG CCC        3498

Lys Aia Leu Tyr Asp Val Ala Glu Ala Glu Glu His Phe Pro Ala Pro
        1000                1005                1010

GCG CGG CCG CGC TCA CCG TCG CCC ATC AGC ACG CTG AGC CAC CGC GCG        3546

Ala Arg Pro Arg Ser Pro Ser Pro Ile Ser Thr Leu Ser His Arg Ala
        1015                1020                1025

GGC TCG GCC AGC CGC ACG GAC GAC GAT GTG CCG TCG CTG CAC TCG GAG        3594

Gly Ser Ala Ser Arg Thr Asp Asp Asp Val Pro Ser Leu His Ser Glu
1030                1035                1040                1045

CCT GTG GCG CGC AGC AGC TCC TCG CAG GGC TCC CTC ATG GAG CAG ATC        3642

Pro Val Ala Arg Ser Ser Ser Gln Gly Ser Leu Met Glu Gln Ile
                1050                1055                1060

AGC AGT GTG GTC ACC CGC TTC ACG GCC AAC ATC AGC GAG CTC AAC TCC        3690

Ser Ser Val Val Thr Arg Phe Thr Ala Asn Ile Ser Glu Leu Asn Ser
        1065                1070                1075

ATG ATG CTG TCC ACC GCG GCC CCC#AGC CCC GGC GTC GGC GCC CCG CTC        3738

Met Met Leu Ser Thr Ala Ala Pro Ser Pro Gly Val Gly Ala Pro Leu
                1080                1085                1090

TGC TCG TCC TAC CTG ATC CCC AAA GAG ATC CAG TTG CCC ACG ACC ATG        3786
```

-continued

```
Cys Ser Ser Tyr Leu Ile Pro Lys Glu Ile Gln Leu Pro Thr Thr Met
    1095                1100                1105

ACG ACC TTT GCC GAA ATC CAG CCT CTG CCG GCC ATC GAA GTC ACG GGC    3834

Thr Thr Phe Ala Glu Ile Gln Pro Leu Pro Ala Ile Glu Val Thr Gly
1110            1115                1120            1125

GGC GCG CAG CCC GCG GCA GGG GCG CAG GCG GCT GGG GAC GCG GCC CGG    3882

Gly Ala Gln Pro Ala Ala Gly Ala Gln Ala Ala Gly Asp Ala Ala Arg
            1130                1135            1140

GAG AGC CCC GCG GCC GGT CCC GAG GCT GCG GCC GCC AAG CCA GAC CTG    3930

Glu Ser Pro Ala Ala Gly Pro Glu Ala Ala Ala Ala Lys Pro Asp Leu
            1145                1150                1155

GAG GAG CTG GTG GCT CTC ACC CCG CCG TCC CCC TTC AGA GAC TCG GTG    3978

Glu Glu Leu Val Ala Leu Thr Pro Pro Ser Pro Phe Arg Asp Ser Val
            1160                1165                1170

GAC TCG GGG AGC ACA ACC CCC AAC TCG CCA GTG TCC GAG TCG GCC CTC    4026

Asp Ser Gly Ser Thr Thr Pro Asn Ser Pro Val Ser Glu Ser Ala Leu
        1175                1180                1185

TGT ATC CCG TCG TCT CCC AAA TAT GAC ACT CTT ATC ATA AGA GAT TAC    4074

Cys Ile Pro Ser Ser Pro Lys Tyr Asp Thr Leu Ile Ile Arg Asp Tyr
1190                1195                1200                1205

ACT CAG AGC TCC TCG CCG CTG TGAATGTCCC TGGAAAGCAC GCCGGCCTGC        4125

Thr Gln Ser Ser Ser Pro Leu
                1210

GCGTGCGGAG CGGAGCCCCC CGTGTTCACA CACACACAAT GGCAAGCATA GCCGCCTGGT   4185

TACGGCCCAG GGGGAAGGTG CCAAGGGCAC CCCTTTATGG AAACACGAGA TCAGTAGCGC   4245

TATCTCATGA CAACCCACGA AGAAACCGAC GACAAATCTC GCGGCAGATT TTCTTCTA     4303
``` hereinafter designated as SEQ ID NO:4.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and adverse reaction profile of agents useful in the treatment or prevention of disorders associated with an excess or deficiency in the amount of glutamate present.

DETAILED DESCRIPTION AND PREFERRED EMBODIMENTS

Figure 1:
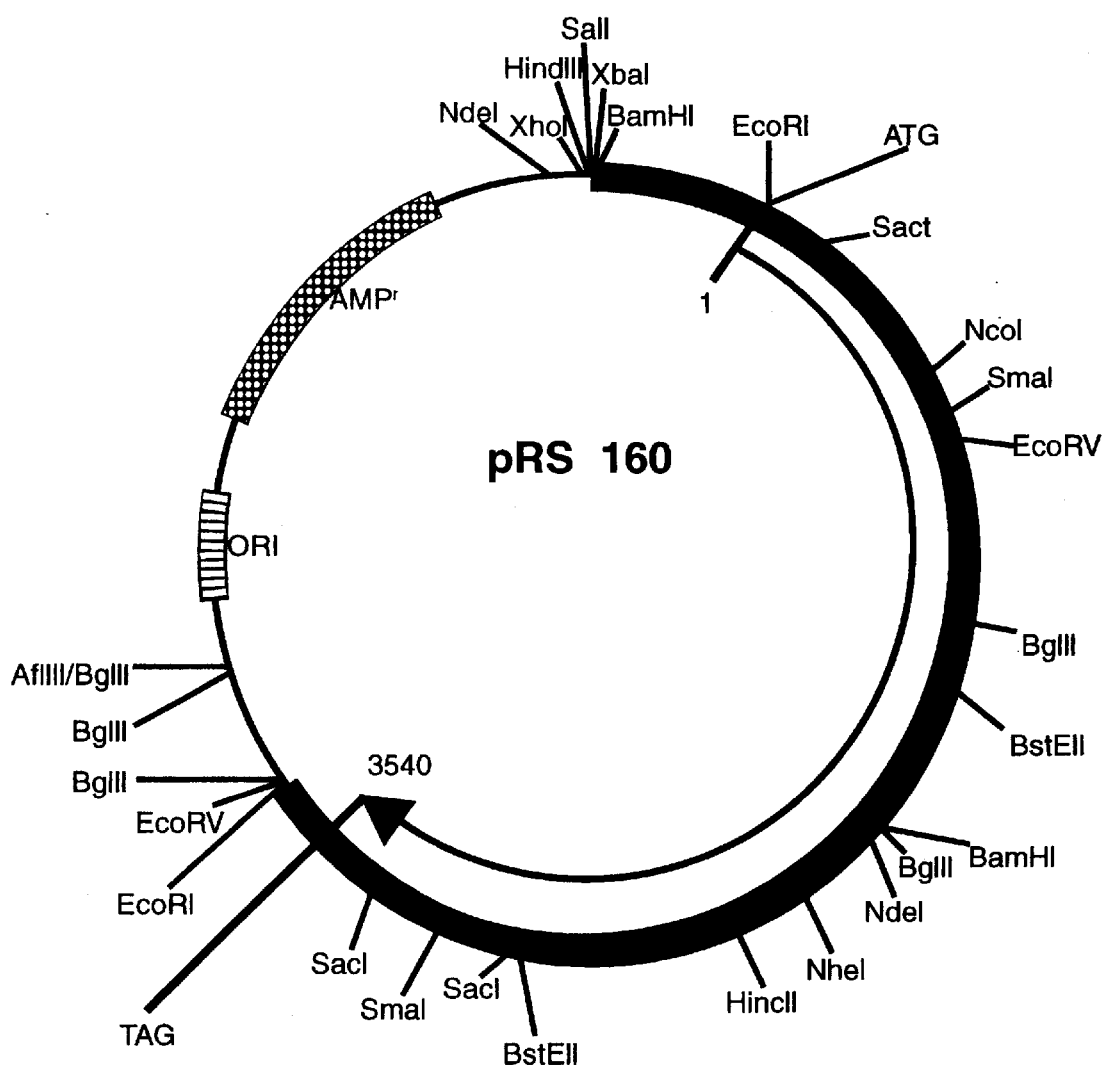
FIG. 1 is a restriction and function map of the plasmid pRS160. The arc having the wider line indicates that portion of the plasmid which corresponds to SEQ ID NO:1, infra. The arrow delineates that region of the insert which encodes the protein of SEQ ID NO:2 with the direction of the arrow indicating the natural order of transcription from the 5' end to the 3' end. The designation "ORI" refers to the plasmid origin of replication. The designation "AMP'" refers to the gene encoding ampicillin resistance.

The terms and abbreviations used in this document have their normal meanings unless otherwise designated. For example "° C." refers to degrees Celsius; "N" refers to normal or normality; "mmole" refers to millimole or millimoles; "g" refers to gram or grams; "ml" means milliliter or milliliters; "M" refers to molar or molarity; "µg" refers to microgram or micrograms; and "µl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments (T. Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases.

The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "PCR" as used herein refers to the widely-known polymerase chain reaction employing a thermally-stable polymerase.

This invention provides the protein of SEQ ID NO:2, a human metabotropic glutamate receptor, designated as a mGluR5 receptor using the nomenclature system described in D. D. Schoepp, "Glutamate receptors", *Handbook of Receptors and Channels*, Chapter 13 (S. J. Peroutka, ed., CRC Press, 1984). This receptor is believed to be found in a large number of tissues throughout the body, including many regions of the brain such as the telencephalic regions, including the cerebral cortex, hippocampus, subiculum, internal granular layer of the olfactory bulb, anterior olfactory nucleus, pyramidal cell layer of the olfactory tubercle, striatum, accumbens nucleus, and lateral septal nucleus. High expression of this mRNA may also be found in the anterior thalanLic nuclei, shell regions of the inferior colliculus, and caudal spinal trigeminal nucleus. This receptor is believed to potentiate central nervous system responses and is, therefore, an important target for pharmaceutical purposes.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See. e.g., H. Dugas and C. Penney, *Bioorganic Chemistry* (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F− (φ80dlacZΔM15), Δ(lacZYA-argF)U169 supE44, λ−, hsdR17($r_K^−$, $m_K^+$), recA1, endA1, gyrA96, thi-1, relA1 |
| HB101 | supE44, hsdS20($r_B^−$ $m_B^−$), recA13, ara-14, proA2 lacY1, galK2, rpsL20, xyl-5, mtl-1, mcrB, mrr |
| JM109 | recA1, e14−(mcrA), supE44, endA1, hsdR17 ($r_K^−$, $m_K^+$), gyrA96, relA1, thi-1, Δ(lac-proAB), F' [traD36, proAB+ lacI$^q$, lacZΔM15] |
| RR1 | supE44, hsdS20 ($r_B^−$ $m_B^−$), ara-14 proA2, lacY1, galK2, rpsL20, xyl-5, mtl-5 |

-continued

| Strain | Genotype |
| --- | --- |
| χ1776 | F⁻, ton, A53, dapD8, minA1, supE42 (glnv42), Δ(gal-uvrB)40, minB2, rfb-2, gyrA25, thyA142, oms-2, metC65, oms-1, Δ(bioH-asd)29, cycB2, cycA1, hsdR2, λ⁻ |
| 294 | endA, thi⁻, hsr⁻, hsm$_k^+$ (U.S. Pat. No. 4,366,246) |

These strains are all commercially available from suppliers such as: Bethesda Research Laboratories, Gaithersburg, Md. 20877 and Stratagene Cloning Systems, La Jolla, Calif. 92037; or are readily available to the poblic from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of E. coli employed in the cloning and expression of the genes of this invention is RV308, which is available from the ATCC under accession number ATCC 31608, and is described in U.S. Pat. No. 4,551,433, issued Nov. 5, 1985.

In addition to the strains of E. coli discussed supra, bacilli such as Bacillus subtilis, other enterobacteriaceae such as Salmonella typhimurium or Serratia marcescans, and various Pseudomonas species may be used. In addition to these gram-negative bacteria, other bacteria, especially Strectomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., Nature (London), 275:615 (1978); and Goeddel et al., Nature (London), 281:544 (1979)], alkaline phosphatase, the tryptophan (trp) promoter system [vector PATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in Protein Purification: From Molecular Mechanisms to Large Scale Processes, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table I

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See. e.a., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, as well as co-pending United States patent application 07/368,700, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BClI site. A depiction of the plasmid phd is provided as FIG. 2 of this document. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the *trp gene* which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPCl (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Skilled artisans also recognize that some alterations of SEQ ID NO:2 or SEQ ID NO:5 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 or SEQ ID NO:5 are shown in Table II, infra.

TABLE II

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 or SEQ ID NO:5 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2 or SEQ ID NO:5. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate mGluR5 receptor molecule may be produced using synthetic methodology. This synthesis of nucleic acids is well known in the art. See, e.g. E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See. e.g., M. J. Gait, ed., *Olgonucleotide Synthesis, A Practical Approach*, (1984).]

The synthetic human glutamate mGluR5 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the mGluR5 receptor molecule. A variety of ther such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence

| | | | | | | | |
|---|---|---|---|---|---|---|---|
| GUGAUACAGA | CCAGUGAGAA | GGCAGCUUCU | CCUUUUCACC | UUCUUCUCCA | UUCGCUACAU | 60 |
| GGGAUUUUAU | UGUUCAGAGU | UUCUCAGGAC | AAAGCUAGAG | CUAAUUUGUG | UCUCUAAUCC | 120 |
| UGGGCACUGG | CCAUUUGAAG | CAGCCAAAGG | UGCAUUGACC | AGGACUACGU | GCAGCCCUUC | 180 |
| CUCCAGUGGG | ACAUAAGCAG | GGGUUUUCUG | UGGAAGUCUU | AGUUGCAUGA | CAUUCUACUG | 240 |
| UCAGCUGUGG | AGUGUUCAGG | UUUAGAAGAU | CAUGACCACA | UGGAUCAUCU | AACUAAAUGG | 300 |
| UACAUGGGGA | CAAAAUGGUC | CUUUAGAAAA | UACAUCUGAA | UUGCUGGCUA | AUUUCUUGAU | 360 |
| UUGCGACUCA | ACGUAGGACA | UCGCUUGUUC | GUAGCUAUCA | GAACCCUCCU | GAAUUCUCCC | 420 |
| CACCUUGCUA | UCUUUAUUGG | CUUGAACUCC | UUUCCUAAAA | UGGUCCUUCU | GUUGAUCCUG | 480 |
| UCAGUCUUAC | UUUUGAAAGA | AGAUGUCCGU | GGGAGUGCAC | AGUCCAGUGA | GAGGAGGGUG | 540 |
| GUGGCUCACA | UGCCGGGUGA | CAUCAUUAUU | GGAGCUCUCU | UUUCUGUUCA | UCACCAGCCU | 600 |
| ACUGUGGACA | AAGUUCAUGA | GAGGAAGUGU | GGGGCGGUCC | GUGAACAGUA | UGGCAUUCAG | 660 |
| AGAGUGGAGG | CCAUGCUGCA | UACCCUGGAA | AGGAUCAAUU | CAGACCCCAC | ACUCUUGCCC | 720 |
| AACAUCACAC | UGGGCUGUGA | GAUAAGGGAC | UCCUGCUGGC | AUUCGGCUGU | GGCCCUAGAG | 780 |
| CAGAGCAUUG | AGUUCAUAAG | AGAUUCCCUC | AUUUCUUCAG | AAGAGGAAGA | AGGCUUGGUA | 840 |
| CGCUGUGUGG | AUGGCUCCUC | CUCUUCCUUC | CGCUCCAAGA | AGCCCAUAGU | AGGGGUCAUU | 900 |
| GGGCUGGCU | CCAGUUCUGU | AGCCAUUCAG | GUCCAGAAUU | UGCUCCAGCU | UUUCAACAUA | 960 |
| CCUCAGAUUG | CUUACUCAGC | AACCAGCAUG | GAUCUGAGUG | ACAAGACUCU | GUUCAAAUAU | 1020 |
| UUCAUGAGGG | UUGUGCCUUC | AGAUGCUCAG | CAGGCAAGGG | CCAUGGUGGA | CAUAGUGAAG | 1080 |
| AGGUACAACU | GGACCUAUGU | AUCAGCCGUG | CACACAGAAG | GCAACUAUGG | AGAAAGUGGG | 1140 |
| AUGGAAGCCU | UCAAAGAUAU | GUCAGCGAAG | GAAGGGAUUU | GCAUCGCCCA | CUCUUACAAA | 1200 |

-continued

| | | | | | | |
|---|---|---|---|---|---|---|
| AUCUACAGUA | AUGCAGGGGA | GCAGAGCUUU | GAUAAGCUGC | UGAAGAAGCU | CACAAGUCAC | 1260 |
| UUGCCCAAGG | CCCGGGUGGU | GGCCUGCUUC | UGUGAGGGCA | UGACGGUGAG | AGGUCUGCUG | 1320 |
| AUGGCCAUGA | GGCGCCUGGG | UCUAGCGGGA | GAAUUUCUGC | UUCUGGGCAG | UGAUGGCUGG | 1380 |
| GCUGACAGGU | AUGAUGUGAC | AGAUGGAUAU | CAGCGAGAAG | CUGUUGGUGG | CAUCACAAUC | 1440 |
| AAGCUCCAAU | CUCCCGAUGU | CAAGUGGUUU | GAUGAUUAUU | AUCUGAAGCU | CCGGCCAGAA | 1500 |
| ACAAACCACC | GAAACCCUUG | GUUUCAAGAA | UUUUGGCAGC | AUCGUUUUCA | GUGCCGACUG | 1560 |
| GAAGGGUUUC | CACAGGAGAA | CAGCAAAUAC | AACAAGACUU | GCAAUAGUUC | UCUGACUCUG | 1620 |
| AAAACACAUC | AUGUUCAGGA | UUCCAAAAUG | GGAUUUGUGA | UCAACGCCAU | CUAUUCGAUG | 1680 |
| GCCUAUGGGC | UCCACAACAU | GCAGAUGUCC | CUCUGCCCAG | GCUAUGCAGG | ACUCUGUGAU | 1740 |
| GCCAUGAAGC | CAAUUGAUGG | ACGGAAACUU | UUGGAGUCCC | UGAUGAAAAC | CAAUUUUACU | 1800 |
| GGGGUUUCUG | GAGAUGCAAU | CCUAUUCGAU | GAGAAUGGAG | ACUCUCCAGG | AAGGUAUGAA | 1860 |
| AUAAUGAAUU | UCAAGGAAAU | GGGAAAAGAU | UACUUUGAUU | AUAUCAACGU | UGGAAGUUGG | 1920 |
| GACAAUGGAG | AAUUAAAAAU | GGAUGAUGAU | GAAGUAUGGU | CCAAGAAAAG | CAACAUCAUC | 1980 |
| AGAUCUGUGU | GCAGUGAACC | AUGUGAGAAA | GGCCAGAUCA | AGGUGAUCCG | AAAGGGAGAA | 2040 |
| GUCAGCUGUU | GUUGGACCUG | UACACCUUGU | AAGGAGAAUG | AGUAUGUCUU | UGAUGAGUAC | 2100 |
| ACAUGCAAGG | CAUGCCAACU | GGGGUCUUGG | CCCACUGAUG | AUCUCACAGG | UUGUGACUUG | 2160 |
| AUCCCAGUAC | AGUAUCUUCG | AUGGGGUGAC | CCUGAACCCA | UUGCAGCUGU | GGUGUUUGCC | 2220 |
| UGCCUUGGCC | UCCUGGCCAC | CCUGUUUGUU | ACUGUAGUCU | UCAUCAUUUA | CCGUGAUACA | 2280 |
| CCAGUAGUCA | AGUCCUCAAG | CAGGGAACUC | UGCUACAUUA | UCCUUGCUGG | CAUCUGCCUG | 2340 |
| GGCUACUUAU | GUACCUUCUG | CCUCAUUGCG | AAGCCCAAAC | AGAUUUACUG | CUACCUUCAG | 2400 |
| AGAAUUGGCA | UUGGUCUCUC | CCCAGCCAUG | AGCUACUCAG | CCCUUGUAAC | AAAGACCAAC | 2460 |
| CGUAUUGCAA | GGAUCCUGGC | UGGCAGCAAG | AAGAAGAUCU | GUACCAAAAA | GCCCAGAUUC | 2520 |
| AUGAGUGCCU | GUGCCCAGCU | AGUGAUUGCU | UUCAUCUCCA | UAUGCAUCCA | GUUGGGCACC | 2580 |
| AUCGUUGCCC | UCUUUAUAAU | GGAGCCUCCU | GACAUAAUGC | AUGACUACCC | AAGCAUUCGA | 2640 |
| GAAGUCUACC | UGAUCUGUAA | CACCACCAAC | CUAGGAGUUG | UCACUCCACU | UGGAUACAAU | 2700 |
| GGAUUGUUGA | UUUUGAGCUG | CACCUUCUAU | GCGUUCAAGA | CCAGAAAUGU | UCCAGCUAAC | 2760 |
| UUCAACGAGG | CCAAGUAUAU | CGCCUUCACA | AUGUACACGA | CCUGCAUUAU | AUGGCUAGCU | 2820 |
| UUUGUGCCAA | UCUACUUUGG | CAGCAACUAC | AAAAUCACCA | CCAUCGUGUUU | CUCGGUCGAC | 2880 |
| CUCAGUGCCA | CAGUGGCCCU | AGGCUGCAUG | UUUGUGCCGA | AGGUGUACAU | CAUCCUGGCC | 2940 |
| AAACCAGAGA | GAAACGUGCG | CAGCGCCUUC | ACCACAUCUA | CCGUGGUGCG | CAUGCAUGUA | 3000 |
| GGGGAUGGCA | AGUCAUCCUC | CGCAGCCAGC | AGAUCCAGCA | GCCUAGUCAA | CCUGUGGAAG | 3060 |
| AGAAGGGCGU | CCUCUGGGGA | AACCUUAAGU | UCCAAUGGAA | AAUCCGUCAC | GUGGGCCCAG | 3120 |
| AAUGAGAAGA | GCAGCCGGGG | GCAGCACCUG | UGGCAGCGCC | UGUCCAUCCA | CAUCAACAAG | 3180 |
| AAAGAAAACC | CCAACCAAAC | GGCCGUCAUC | AAGCCCUUCC | CCAAGAGCAC | GGAGAGCCGU | 3240 |
| GGCCUGGGCG | CUGGCGCUGG | CGCAGGCGGG | AGCGCUGGGG | GCGUGGGGGC | CACGGGCGGU | 3300 |
| GCGGGCUGCG | CAGGCGCCGG | CCCAGGCGGG | CCCCAAGGCG | CCCCAAGGCG | CCCCAAGGCG | 3360 |
| CUGUAUGAUG | UGGCCGAGGC | UGAGGAGCAC | UUCCCGGCGC | CCGCGCGGCC | GCGCUCACCG | 3420 |
| UCGCCCAUCA | GCACGCUGAG | CCACCGCGCG | GGCUCGGCCA | GCCGCACGGA | CGACGAUGUG | 3480 |
| CCGUCGCUGC | ACUCGGAGCC | UGUGGCGCGC | AGCAGCUCCU | CGCAGGGCUC | CCUCAUGGAG | 3540 |
| CAGAUCAGCA | GUGUGGUCAC | CCGCUUCACG | GCCAACAUCA | GCGAGCUCAA | CUCCAUGAUG | 3600 |
| CUGUCCACCG | CGGCCCCCAG | CCCCGGCGUC | GGCGCCCCGC | UCUGCUCGUC | CUACCUGAUC | 3660 |
| CCCAAAGAGA | UCCAGUUGCC | CACGACCAUG | ACGACCUUUG | CCGAAAUCCA | GCCUCUGCCG | 3720 |
| GCCAUCGAAG | UCACGGGCGG | CGCGCAGCCC | GCGGCAGGGG | CGCAGGCGGC | UGGGGACGCG | 3780 |
| GCCCGGGAGA | GCCCCGCGGC | CGGUCCGAGG | GCUGCGGCCG | CCAAGCCAGA | CCUGGAGGAG | 3840 |
| CUGGUGGCUC | UCACCCCGCC | GUCCCCCUUC | AGAGACUCGG | UGGACUCGGG | GAGCACAACC | 3900 |
| CCCAACUCGC | CAGUGUCCGA | GUCGGCCCUC | UGUAUCCCGU | CGUCUCCCAA | AUAUGACACU | 3960 |
| CUUAUCAUAA | GAGAUUACAC | UCAGAGCUCC | UCGCCGCUGU | GAAUGUCCCU | GGAAAGCACG | 4020 |
| CCGGCCUGCG | CGUGCGGAGC | GGAGCCCCCC | GUGUUCACAC | ACACACAAUG | GCAAGCAUAG | 4080 |
| CCGCCUGGUU | ACGGCCCAGG | GGGAAGGUGC | CAAGGGCACC | CCUUUAUGGA | AACACGAGAU | 4140 |
| CAGUAGCGCU | AUCUCAUGAC | AACCCACGAA | GAAACCGACG | ACAAAUCUCG | CGGCAGAUUU | 4200 |
| UCUUCUA | 4207 | | | | | | hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template.

In addition to the deoxyribonucleic acid of SEQ ID NO:4, this invention also provides ribonucleic acids (RNA) which comprise the RNA sequence

| | | | | | | |
|---|---|---|---|---|---|---|
| GUGAUACAGA | CCAGUGAGAA | GGCAGCUUCU | CCUUUUCACC | UUCUUCUCCA | UUCGCUACAU | 60 |
| GGGAUUUUAU | UGUUCAGAGU | UUCUCAGGAC | AAAGCUAGAG | CUAAUUUGUG | UCUCUAAUCC | 120 |
| UGGGCACUGG | CCAUUUGAAG | CAGCCAAAGG | UGCAUUGACC | AGGACUACGU | GCAGCCCUUC | 180 |
| CUCCAGUGGG | ACAUAAGCAG | GGGUUUUCUG | UGGAAGUCUU | AGUUGCAUGA | CAUUCUACUG | 240 |
| UCAGCUGUGG | AGUGUUCAGG | UUUAGAAGAU | CAUGACCACA | UGGAUCAUCU | AACUAAAUGG | 300 |
| UACAUGGGGA | CAAAAUGGUC | CUUUAGAAAA | UACAUCGAAU | UUGCUGGCUA | AUUUCUUGAU | 360 |
| UUGCGACUCA | ACGUAGGACA | UCGCUGUUC | GUAGCAUCA | GAACCCUCCU | GAAUUCUCCC | 420 |
| CACCUUGCUA | UCUUUAUUGG | CUUGAACUCC | UUUCCUAAAA | UGGUCCUUCU | GUUGAUCCUG | 480 |
| UCAGUCUUAC | UUUUGAAAGA | AGAUGCCGU | GGGAGUGCAC | AGUCCAGUGA | GAGGAGGGUG | 540 |
| GUGGCUCACA | UGCCGGGUGA | CAUCAUUAUU | GGAGCUCUCU | UUUCUGUUCA | UCACCAGCCU | 600 |
| ACUGGGACA | AAGUUCAUGA | GAGGAAGUGU | GGGGCGGUCC | GUGAACAGUA | UGGCAUUCAG | 660 |
| AGAGUGGAGG | CCAUGCUGCA | UACCCUGGAA | AGGAUCAAUU | CAGCCCCAC | ACUCUUGCCC | 720 |
| AACAUCACAC | UGGGCUGUGA | GAUAAGGGAC | UCCUGCUGGC | AUUCGGCUGU | GGCCCUAGAG | 780 |
| CAGAGCAUUG | AGUUCAUAAG | AGAUUCCCUC | AUUUCUUCAG | AAGAGGAAGA | AGGCUUGGUA | 840 |

-continued

| | | | | | | |
|---|---|---|---|---|---|---|
| CGCUGUGUGG | AUGGCUCCUC | CUCUUCCUUC | CGCUCCAAGA | AGCCCAUAGU | AGGGGUCAUU | 900 |
| GGGCCUGGCU | CCAGUUCUGU | AGCCAUUCAG | GUCCAGAAUU | UGCUCCAGCU | UUUCAACAUA | 960 |
| CCUCAGAUUG | CUUACUCAGC | AACCAGCAUG | GAUCCAGACU | ACAAGACUCU | GUUCAAAUAU | 1020 |
| UUCAUGAGGG | UUGUGCCUUC | AGAUGCUCAG | CAGGCAAGGG | CCAUGGUGGA | CAUAGUGAAG | 1080 |
| AGGUACAACU | GGACCUAUGU | AUCAGCCGUG | CACACAGAAG | GCAACUAUGG | AGAAAGUGGG | 1140 |
| AUGGAAGCCU | UCAAAGAUAU | GUCAGCGAAG | GAAGGGAUUU | GCAUCGCCCA | CUCUUACAAA | 1200 |
| AUCUACAGUA | AUGCAGGGGA | GCAGAGCUUU | GAUAAGCAGU | UGAAGAAGCU | CACAAGUCAC | 1260 |
| UUGCCCAAGG | CCCGGGUGGU | GGCCUGCUUC | UGUGAGGGCA | UGACGGUGAG | AGGUCUGCUG | 1320 |
| AUGGCCAUGA | GGCGCCUGGG | UCUAGCGGGA | GAAUUUCUGC | UUCUGGGCAG | UGAUGGCUGG | 1380 |
| GCUGACAGGU | AUGAUGUGAC | AGAUGGAUAU | CAGCGAGAAG | CUGUUGGUGG | CAUCACAAUC | 1440 |
| AAGCUCCAAU | CUCCCGAUGU | CAAGUGGUUU | GAUGAUUAUU | AUCUGGAAGCU | CCGGCCAGAA | 1500 |
| ACAAACCACC | GAAACCCUUG | GUUUCAAGAA | UUUUGGCAGC | AUCGUUUUCA | GUGCCGACUG | 1560 |
| GAAGGGUUUC | CACAGGAGAA | CAGCAAAUAC | AACAAGACUU | GCAAUAGUUC | UCUGACUCUG | 1620 |
| AAAACACAUC | AUGUUCAGGA | UUCCAAAAUG | GGAUUUGUGA | UCAACGCCAU | CUAUUCGAUG | 1680 |
| GCCUAUGGGC | UCCACAACAU | GCAGAUGUCC | CUCUGCCCAG | GCUAUGCAGG | ACUCUGUGAU | 1740 |
| GCCAUGAAGC | CAAUUGAUGG | ACGGAAACUU | UUGGAGUCCC | UGAUGAAAAC | CAAUUUUACU | 1800 |
| GGGGUUUCUG | GAGAUACGAU | CCUAUUCGAU | GAGAAUGGAG | ACUCUCCAGG | AAGGUAUGAA | 1860 |
| AUAAUGAAUU | UCAAGGAAAU | GGGAAAAGAU | UACUUUGAUU | AUAUCAACGU | UGGAAGUUGG | 1920 |
| GACAAUGGAG | AAUUAAAAAU | GGAUGAUGAU | GAAGUAUGGU | CCAAGAAAAG | CAACAACAUC | 1980 |
| AGAUCUGUGU | GCAGUGAACC | AUGUGAGAAA | GGCCAGAUCA | AGGUGAUCCG | AAAGGGAGAA | 2040 |
| GUCAGCUGUU | GUUGGACCUG | UACACCUUGU | AAGGAGAAUG | AGUAUGUCUU | UGAUGAGUAC | 2100 |
| ACAUGCAAGG | CAUGCCAACU | GGGGUCUUGG | CCCACUGAUG | AUCUCACAGG | UUGUGACUUG | 2160 |
| AUCCCAGUAC | AGUAACUUCG | AUGGGUGAC | CCUGAACCCA | UUGCAGCUGU | GGUGUUUGCC | 2220 |
| UGCCUUGGCC | UCCUGGCCAC | CCUGUUUGUU | ACUGUAGUCU | UCAUCAUUUA | CCGUGAUACA | 2280 |
| CCAGUAGUCA | AGUCCUCAAG | CAGGGAACUC | UGCUACAUUA | UCCUUGCUGG | CAUCUGCCUG | 2340 |
| GGCUACUUAU | GUACCUUCUG | CCUCAUUGCG | AAGCCCAAAC | AGAUUUACUG | CUACCUUCAG | 2400 |
| AGAAUUGGCA | UUGGUCUCUC | CCCAGCCAUG | AGCUACUCAG | CCCUUGUAAC | AAAGACCAAC | 2460 |
| CGUAUUGCAA | GGAUCCUGGC | UGGCCAAGG | AAGAAGAUCU | GUACCAAAAA | GCCCAGAUUC | 2520 |
| AUGAGUGCCU | GUGCCCAGCU | AGUGAUUGCU | UUCAUUCUCA | UAUGCAUCCA | GUUGGGCAUC | 2580 |
| AUCGUUGCCC | UCUUUAUAAU | GGAGCCUCCU | GACAUAAUGC | AUGACUACCC | AAGCAUUCGA | 2640 |
| GAAGUCUACC | UGAUCUGUAA | CACCACCAAC | CUAGGAGUUG | UCACUCCACU | UGGAUACAAU | 2700 |
| GGAUUGUUGA | UUUUGAGCUG | CACCUUCUAU | GCGAUUACAG | CCAGAAAUGU | UCCAGCUAAC | 2760 |
| UUCAACGAGG | CCAAGUAUAU | CGCCUUCACA | AUGUACACGA | CCUGCAUUAU | AUGGCUAGCU | 2820 |
| UUUGUGCCAA | UCUACUUUGG | CAGCAACUAC | AAAAUCAUCA | CCAUGUGUUU | CUCGGUCAGC | 2880 |
| CUCAGUGCCA | CAGUGGCCCU | AGGCUGCAUG | UUUGUGCCGA | AGGUGUACAU | CAUCCUGGCC | 2940 |
| AAACCAGAGA | GAAACGUGCG | CAGCGCCUUC | ACCACAUCUA | CCGUGGUGCG | CAUGCAUGUA | 3000 |
| GGGGAUCGCA | AGUCAUCCUC | CGCAGCCAGC | AGAUCCAGCA | GCCUAGUCAA | CCUGUGGAAG | 3060 |
| AGAAGGGGCU | CCUCUGGGGA | AACCUUAAGG | UACAAAGACA | GGAGACUGGC | CCAGCACAAG | 3120 |
| UCGGAAAUAG | AGUGUUUCAC | CCCCAAAGGG | AGUAUGGGGA | AUGGUGGGAG | AGCAACAAUG | 3180 |
| AGCAGUUCCA | AUGGAAAAUC | CGUCACGUGG | GCCCAGAAUG | AGAAGAGCAG | CCGGGGGCAG | 3240 |
| CACCUGUGGC | AGCGCCUGUC | CAUCCACAUC | AACAAGAAAG | AAAACCCCAA | CCAAACGGCC | 3300 |
| GUCAUCAAGC | CCUUCCCCAA | GAGCACGGAG | AGCCGUGGCC | UGGGCGCUGG | CGCUGGCGCA | 3360 |
| GGCGGGAGCG | CUGGGGGCGU | GGGGGCCACG | GGCGGUGCGG | GCUGCGCAGG | CGCCGGCCCA | 3420 |
| GGCGGGCCCG | AGUCCCCAGA | CGCCGGCCCC | AAGGCGCUGU | AUGAUGGGCC | CGAGGCGUAG | 3480 |
| GAGCACUUCC | CGGCGCCCGC | GCGGCCGCGC | UCACCGUCGC | CCAUCAGCAC | GCUGAGCCAC | 3540 |
| CGCGCGGGCU | CGGCCAGCCG | CACGGACGAC | GAUGUGCCGU | CGCUGCACUC | GGAGCCUGUG | 3600 |
| GCGCGCAGCA | GCUCCUCGCA | GGGCUCCCUC | AUGGAGCAGA | UCAGCAGUGU | GGUCACCCGC | 3660 |
| UUCACGGCCA | ACACCAGCGA | GCUCAACCUC | AUGAUGCGU | CCACCGCGGC | CCCCAGCCCC | 3720 |
| GGCGUCGGCG | CCCCGCUCUG | CUCGUCCUAC | CUGAUCCCCA | AAGAGAUCCA | GUUGCCCACG | 3780 |
| ACCAUGACGA | CCUUUGCCGA | AAUCCAGCCU | CUGCCGGCCA | UCGAAGUCAC | GGGCGGCGCG | 3840 |
| CAGCCCGCGG | CAGGGGCGCA | GGCGGCUGGG | GACGCGGCCC | GGGAGAGCCC | CGCGGCCGGU | 3900 |
| CCCGAGGCUG | CGGCCGCCAA | GCCAGACCUG | GAGGAGCUGG | UGGCUCUCAC | CCCGCCGUCC | 3960 |
| CCCUUCAGAG | ACUCGGUGGA | CUCGGGGAGC | ACAACCCCA | ACUCGCCAGU | GCUCGCCGAG | 4020 |
| GCCCUCUGUA | UCCCGUCGUC | UCCCAAAUAU | GACACUCUUA | UCAAGAGAGA | UUACACUCAG | 4080 |
| AGCUCCUCGC | CGCUGUGAAU | GUCCCUGGAA | AGCACGCCGG | CCUGCGCGUG | CGGAGCGGAG | 4140 |
| CCCCCCGUGU | UCACACACAC | ACAAUGGCAA | GCAUAGCCGC | CUGGUUACGG | CCCAGGGGGA | 4200 |
| AGGUGCCAAG | GGCACCCCUU | UAUGGAAACA | CGAGACAGU | AGCGCUAUCU | CAUGCAACC | 4260 |
| CACGAAGAAA | CCGACGACAA | AUCUCGCGGC | AGAUUUCUU | CUA | | 4303 | hereinafter referred to as SEQ ID NO:6, or the complementary ribonucleic acid, or a fragment of either SEQ ID NO:6 or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1, SEQ ID NO:3, SEQ ID NO:4, or SEQ ID NO:6.

The present invention also provides probes and primers useful for molecular biology techniques. A compound which encodes for SEQ ID NO:1, SEQ ID NO:3, a complementary sequence of either SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The present invention also provides probes and primers useful for molecular biology techniques. A compound which encodes for SEQ ID NO:4, SEQ ID NO:6, a complementary sequence of either SEQ ID NO:4 or SEQ ID NO:6, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The term "selectively hybridize" as used herein may refer to either of two situations. In the first such embodiment of this invention, the nucleic acid compounds described supra hybridize to a human glutamate receptor under more stringent hybridization conditions than these same nucleic acid compounds would hybridize to an analogous glutamate receptor of another species, e.g. murine or primate. In the second such embodiment of this invention, these probes hybridize to-the mGluR5 receptor under more stringent hybridization conditions than other related compounds, including nucleic acid sequences encoding other glutamate receptors.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1 or SEQ ID NO:4. Plasmid pRS160, which has been deposited with the NRRL and is available under accession number NRRL B-21175, is an especially preferred DNA vector of the present invention. Plasmid pRS161, which has been deposited with the NRRL and is available under accession number NRRL B-21176, is another especially preferred DNA vector of the present invention.

The plasmids pRS160 and pRS 161 were prepared by hybridizing to a human fetal brain cDNA library (commercially available from Stratagene, Inc.) a radiolabeled probe derived from the sequence of a rat mGluR5 receptor as published in T. Abe, et al., *Journal of Biological Chemistry*, 267:13361–13368 (1992). A region of this sequence bearing little homology to the sequences of other glutamate receptors was employed. This probe, about 370 bp in the rat sequence, was labeled with [$\alpha$-$^{32}$P]-deoxynucleosidetriphosphate using primers and the polymerase chain reaction. This labeled probe was hybridized to the human fetal brain cDNA library under low stringency conditions (30° C., 30% formamide) to isolate a number of clones having homologous sequences.

The original human fetal brain cDNA library, with a complexity of 2×10$^6$ independent clones, was divided into 100 sublibraries by plating and separately harvesting 100 plates of 50,000 plaque forming unites (pfu) each. Aliquots of the 20 pools were evaluated using two other primers with standard PCR conditions followed by agarose gel electrophoresis. Nineteen of the twenty pools were found to be positive for mGluR5 sequences indicating that the gene was fairly abundant in the library.

Individual plaques, containing the sequences of interest were obtained using standard plaque hybridization on nylon membrane, using the ~370 bp probe described, supra. Small (2 ml) liquids lysates were prepared from the 17 clones identified by the hybridization procedure.

None of these clones contained a full length gene encoding the protein of interest. The 5' terminus of the mRNA, containing the initiating ATG codon as well as some 5' untranslated sequences, was obtained from one of these clones. The 3' termini of the mRNA was then obtained using the information gathered from the 5' terminal region.

Sequencing of these clones revealed two forms of the mGluR5 receptor, presumably arising from alternative splicing of the messenger RNA. The first such cDNA is depicted in SEQ ID NO:1 and results in a receptor known as the mGluR5A receptor, the protein of SEQ ID NO:2. The second such cDNA (depicted in SEQ ID NO:4) contains ninety-six more basepairs and results in the mGluR5B receptor of SEQ ID NO:5.

After cloning the entire coding regions into plasmids, the sequences were further modified by site-directed mutagenesis at the 5' end upstream of the initiating methionine (ATG) codon (position 460 in SEQ ID NO:1 and SEQ ID NO:4). An EcoRI restriction site was introduced by changing basepair 416 from $T_{416}$ to $C_{416}$ and a cryptic ATG at basepair 425 was destroyed by changing $A_{425}$ to $T_{425}$.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

Figure 2:
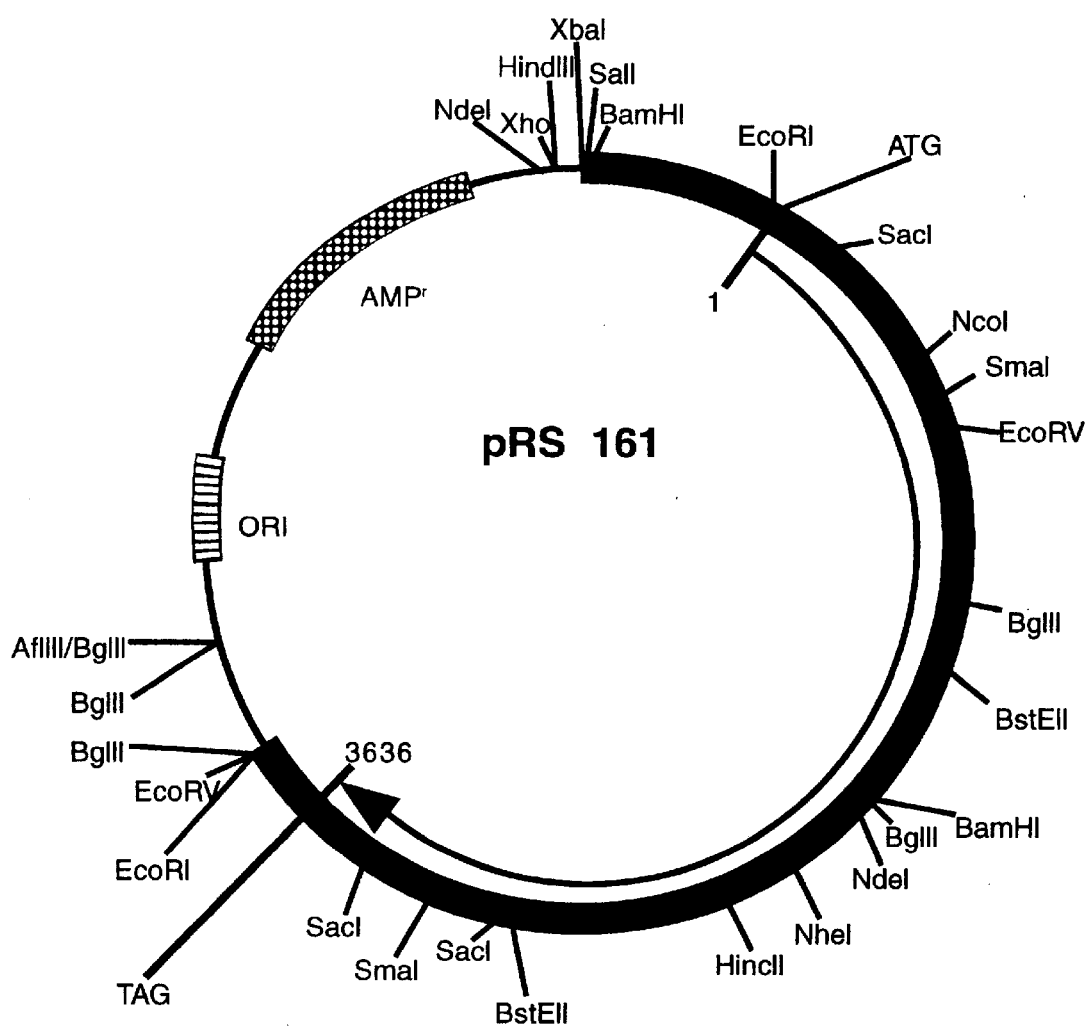
FIG. 2 is a restriction and function map of the plasmid pRS161. The arc having the wider line indicates that protion of the plasmid which corresponds to SEQ ID NO:2, infra. The arrow delineates that region of the insert which encodes the protein of SEQ ID NO:4 with the direction of the arrow indicating the natural order of transcription from the 5' end to the 3' end. The designation "ORI" refers to the plasmid origin of replication. The designation "AMP'" refers to the gene encoding ampicillin resistance.
Figure 3:
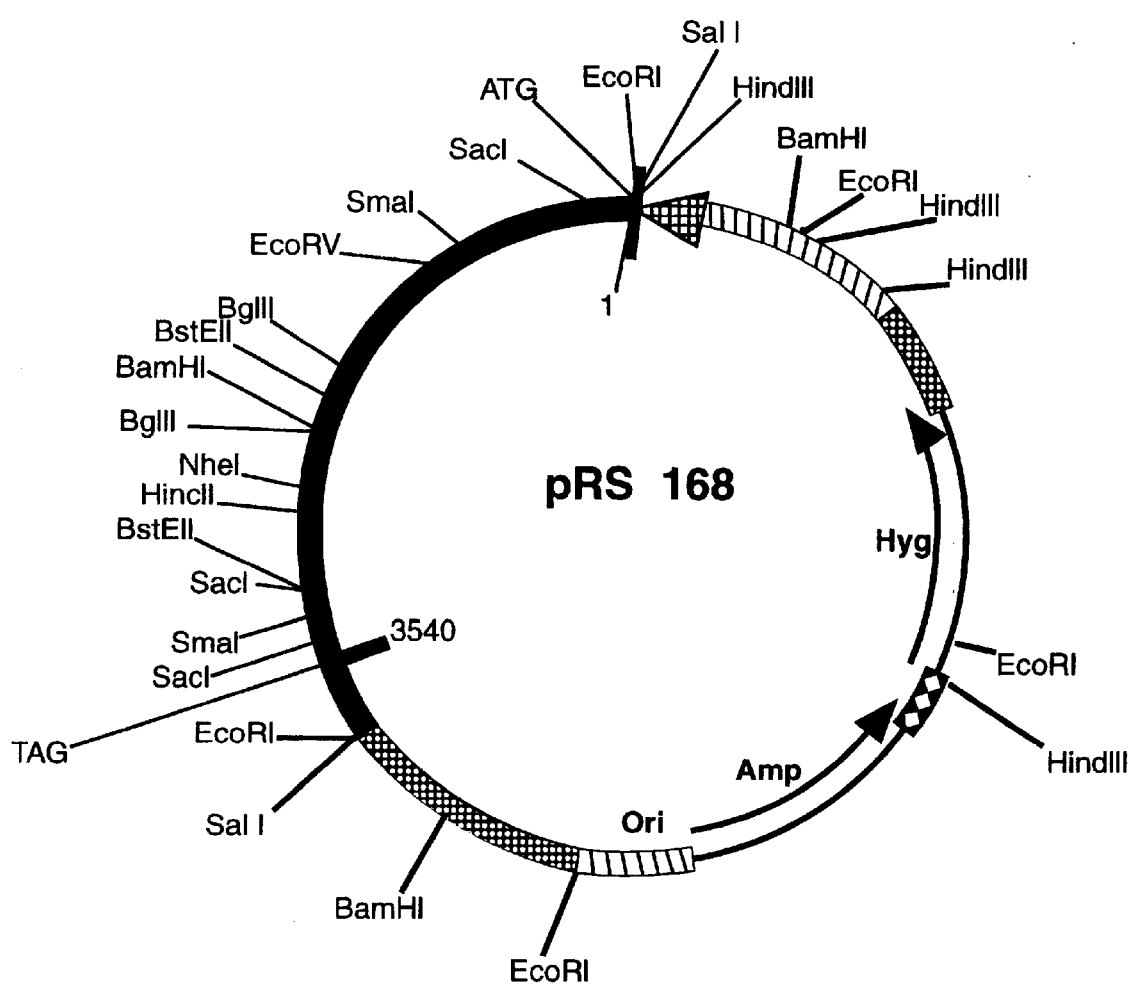
FIG. 3 is a restriction and function map of the plasmid pRS168. The arc having the wider line indicates that portion of the plasmid which corresponds to SEQ ID NO:1, infra. The arrow delineates that region of the insert which encodes the protein of SEQ ID NO:2 with the direction of the arrow indicating the natural order of transcription from the 5' end to the 3' end. The region between the 3' end of the mGluR5A gene and the ori region is the poly-adenylation region derived from simian virus 40 (SV40). The region between the distal end of the ampicillin resistance gene and the hygromycin resistance gene is a promoter enhancer region derived from the SV40 early promoter. The region culminating in the arrowhead consititutes a promoter region derived from the enhancer region of the BK virus, and a promoter derived from an adenovirus middle late promoter. The designation "AMP" refers to the gene encoding ampicillin resistance. The designation "Hyg" refers to the gene encoding hygromycin resistance.

Plasmids pRS160 and pRS161 may be isolated from the deposited *E. coli* containing these plasmids using standard procedures such as cesium chloride DNA isolation. Cleaving of pRS160 with the restriction enzyme EcorI yields a four kilobasepair fragment comprising SEQ ID NO:2. Similar cleavage of pRS161 releases a 4.1 kilobase pair DNA fragment comprising SEQ ID NO:4. The relative locations of these restriction sites and the direction of translation of the proteins of the instant invention are depicted in FIGS. 1 and 2.

Plasmids pRS160 and pRS 161 are readily modified to construct expression vectors that produce mGluR5 receptors in a variety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2 or SEQ ID NO:5, said method comprising transforming a host cell with a recombinant DNA vector that comprises an isolated DNA sequence which encodes SEQ ID NO:2 or SEQ ID NO:5. The preferred host cell is AV12. The preferred vector for expression is one which comprises SEQ ID NO:1 or SEQ ID NO:4. Another preferred host cell for this method is *E. coli*. An especially preferred expression vector in *E. coli* is one which comprises SEQ ID NO:1 or SEQ ID NO:4. Transformed host cells may be cultured under conditions well known to skilled artisans such that SEQ ID NO:2 or SEQ ID NO:5 is expressed, thereby producing mGluR5 in the recombinant host cell.

The ability of glutamate to bind to the mGluR5 receptor is essential in the development of a multitude of indications. In developing agents which act as antagonists or agonists of the mGluR5 receptor, it would be desirable, therefore, to determine those agents which bind the mGluR5 receptor. Generally, such an assay includes a method for determining whether a substance is a functional ligand of the mGluR5 receptor, said method comprising contacting a functional compound of the mGluR5 receptor with said substance, monitoring binding activity by physically detectable means, and identifying those substances which effect a chosen response. Preferably, the physically detectable means is competition with labeled glutamate or binding of ligand in an oocyte transient expression system The instant invention provides such a screening system useful for discovering agents which compete with glutamate for binding to the mGluR5 receptor, said screening system comprising the steps of:

a) isolating a human mGluR5 receptor;

b) exposing said human mGluR5 receptor to a potential inhibitor or surrogate of the glutamate/mGluR5 receptor complex;

c) introducing glutamate;

d) removing non-specifically bound molecules; and e) quantifying the concentration of bound potential inhibitor and/or glutamate.

This allows one to rapidly screen for inhibitors or surrogates of the formation of the glutamate/mGluR5 receptor complex. Utilization of the screening system described above provides a sensitive and rapid means to determine compounds which interfere with the formation of the glutamate/mGluR5 receptor complex. This screening system may also be adapted to automated procedures such as a Pandex® (Baxter-Dade Diagnostics) system allowing for efficient high-volume screening of potential therapeutic agents.

In such a screening protocol a mGluR5 receptor is prepared as elsewhere described herein, preferably using recombinant DNA technology. A sample of a test compound is then introduced to the reaction vessel containing the mGluR5 receptor followed by the addition of glutamate. In the alternative the glutamate may be added simultaneously with the test compound. Unbound molecules are washed free and the eluent inspected for the presence of glutamate or the test compound.

For example, in a preferred method of the invention, radioactively or chemically labeled glutamate may be used. The eluent is then scored for the chemical label or radioactivity. The absence or diminution of the chemical label or radioactivity indicates the formation of the glutamate/mGluR5 receptor complex. This indicates that the test compound has not effectively competed with glutamate in the formation of the glutamate/mGluR5 receptor complex. The presence of the chemical label or radioactivity indicates that the test compound has competed with glutamate in the formation of the glutamate/mGluR5 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan these assays may also be performed such that the practitioner measures the radioactivity or fluorescence remaining with the protein, not in the eluent. A preferred such assay employs radiolabeled glutamate. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The mGluR5 receptor may be free in solution or bound to a solid support. Whether the mGluR5 receptor is bound to a support or is free in solution, it is generally important that the conformation of the protein be conserved. In a preferred practice of the invention, therefore, the mGluR5 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to mGluR5 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H]glutamate to the human mGluR5 receptor of the present invention.

In this assay suspension cells stably expressing the cloned human mGluR5 receptor are harvested by centrifugation at 2200×g for 15 minutes at 4° C. Membranes for the binding assays are prepared by vortexing the cell pellet in 50 mM Tris.HCl, pH 7.4 (0.5×10$^9$ cells/30 ml). The tissue suspension is then centrifuged at 39,800×g for 10 minutes at 4° C. This procedure is repeated for a total of three washes, with a 10 minute incubation at 37° C. between the second and third washes. The final pellet is homogenized in 67 mM Tris.HCl, pH 7.4, at 12.5×10$^6$ cells/ml using a Tissumizer® (Tekmar, Cincinati, Ohio) at setting 65 for 15 seconds.

Binding assays are performed in triplicate in 0.8 ml total volume. Volumes of 200 µl of membrane suspension (0.07–0.10 mg of protein) and 200 µl of drug dilution in water are added to 400 µl of 67 mM of Tris.HCl, pH 7.4, containing [$^3$H]glutamate (35 nM final concentration, 23.7 Ci/mole), calcium chloride (3 mM), pargyline (10 µM, and L-ascorbic acid (5.7 nM). The reaction mixtures are incubated at 37° C. for 15 minutes and then rapidly filtered, using a Brandel™ cell harvester (Model MB-48R; Brandel, Gaithersburg, Md.) over Whatman GF/B filters that had been presoaked in 0.5% polyethyleneimine and precooled with ice-cold 50 mM Tris.HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from 10$^{-5}$ to 10$^{-10}$ M. The IC$_{50}$ values are determined by nonlinear regression analysis (Systat™; Systat Inc., Evanston, Ill.) which may be converted to $K_i$ values using the Cheng-Prusoff equation. Y. Cheng and W. H. Prusoff, *Biochemical Pharmacology*, 22:3099–3108 (1973).

In this particular type of competition assay the following compounds are frequently used.

(a) Quisqualate—a compound of the formula

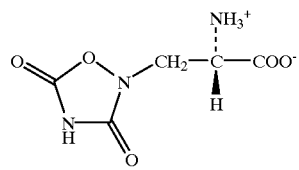

having the chemical name (S)-α-amino-3,5-dioxo-1,2,4-oxadiazolidine-2-propanoate. This compound can be prepared as described in J. E. Baldwin, et al., *Chemical Communications*, 256 (1985).

(b) Glutamate—a compound of the formula

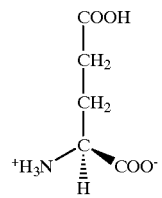

having the chemical name 1-aminopropane-1,3-dicarboxylate. This compound is readily available and can be purchased commercially from several sources.

(c) Ibotenate—a compound of the formula

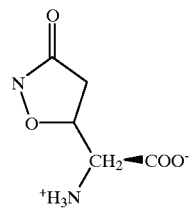

having the chemical name α-amino-3-hydroxy-5-isoxazoleacetate, which can be prepared as described in U.S. Pat. No. 3,459,862, herein incorporated by reference.

(d) t-ACPD—a compound of the formula

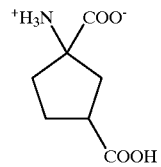

having the chemical name 1-aminocyclopentane-1,3-dicarboxylate. This compound can be purchased commercially from several sources.

The previously described screening system identifies compounds which competitively bind to the mGluR5 receptor. Determination of the ability of such compounds to stimulate or inhibit the action of the mGluR5 receptor is essential to further development of such compounds for therapeutic applications. The need for a bioactivity assay system which determines the response of the mGluR5 receptor to a compound is clear. The instant invention provides such a bioactivity assay, said assay comprising the steps of:

a) transfecting a mammalian host cell with an expression vector comprising DNA encoding a mGluR5 receptor;

b) culturing said host cell under conditions such that the DNA encoding the mGluR5 receptor is expressed, c) exposing said host cell so transfected to a test compound, and d) measuring the change in a physiological condition known to be influenced by the binding of glutamate to the mGluR5 receptor relative to a control in which the transfected host cell is exposed to glutamate.

An oocyte transient expression system can be constructed according to the procedure described in S. Lubbert, et al., *Proceedings of the National Academy of Sciences (USA)*, 84:4332 (1987).

In an especially preferred embodiment of this invention an assay which correlates glutamate activity with the hydrolysis of phosphatidylinositol was performed. The hydrolysis of phosphatidylinositol is known to positively correlate with addition of glutamate. This biochemical assay was performed essentially as described by M. Berridge, *Biochemistry Journal*, 212:849 (1983).

Phosphatidylinositol Assay

Phosphatidylinositol hydrolysis in clonal cell lines of AV12/pRS168 cells was measured in response to glutamate agonists as a functional assay for metabotropic glutamate receptor activity according to D. Schoepp, *Trends in Pharmaceutical Sciences*, 11:508 (1990).

Twenty-four-well tissue-culture vessels were seeded with approximately 250,000 cells per well in Dulbecco's Minimal Essential Media (D-MEM) (in the absence of glutamic acid) which contained 2 mM glutamine and 10% dialyzed fetal calf serum. After 24 hours growth at 37° C. the media was removed and replaced with fresh media containing four microcuries of [$^3$H]myoinositol per well and the cultures were incubated a further 16 to 20 hours. The media was then removed and the cells in each well were washed with serum free medium containing 10 mM lithium chloride, 10 mM myoinositol, and 10 mM HEPES (2×1 ml washes). After the final wash, 0.5 ml of washing solution was added containing the appropriate concentrations fo drugs and vehichles.

If the particular assay was testing antagonists, a ten minute incubation was performed prior to agonist induction. Cells were incubated for about one hour at 37° C. in 95%/5% $O_2/CO_2$ or as appropriate for time course. The reactions were terminated by removing media and adding 1 ml of coled 1:1 acetone:methanol followed by induction on ice for a minimum of twenty minutes.

These extracts were then removed and placed in 1.5 ml centrifuge tubes. Each well was washed with 0.5 ml water and this wash was added to the appropriate extract. After mixing and centrifugation, each aqueous supernatant was processed by chromatography on a QMA SEP-PAK® column, which had previously been wetted and equilibrated by passing 10 ml of water, followed by 8 ml of 1 M triethylammonium hydrogen carbonate (TEAB), followed by 10 ml of water through the column.

The assay supernatants contining the water soluble [$^3$H] inositol phosphate were passed over the columns. This was followed by a 10 ml water wash and a 4 ml wash with 0.02 MTEAB to remove [$^3$H]inositol precursors. [$^3$H]Inositol phosphate was eluted with 4 ml of 0.1 M TEAB into scintillation vials and counted in the presence of scintillation cocktail. Total protein in each sample was measured using standard techniques. Assays were measured as the amount of [$^3$H]inositol phosphate release per milligram of protein.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See. e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$',and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of mGluR5 receptors.

In addition to being functional as direct therapeutic and diagnostic aids, the availability of a family of antibodies which are specific for the mGluR5 receptor enables the development of numerous assay systems for detecting agents which bind to this receptor. One such assay system comprises radiolabeling mGluR5 receptor-specific antibodies with a radionuclide such as $^{125}I$ and measuring displacement of the radiolabeled mGluR5 receptor-specific antibody from solid phase mGluR5 receptor in the presence of a potential antagonist.

Numerous other assay systems are also readily adaptable to detect agents which bind mGluR5 receptor. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the mGluR5 receptor, this invention also provides antibodies which are specific for the hypervariable regions of the anti-mGluR5 receptor antibodies. Some such anti-idiotypic antibodies would resemble the original epitope, the mGluR5 receptor, and, therefore, would be useful in evaluating the effectiveness of compounds which are potential antagonists, agonists, or partial agonists of the mGluR5 receptor. See, e.g., Cleveland, et al., *Nature (London)*, 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-mGluR5 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

Culture Deposits

Under the provisions of the Budapest Treaty on the International Recognition of the Deposit of Microorganisms for Purposes of Patent Procedures, the following cultures have been deposited with the permanent culture collection of the Northern Regional Research Laboratories (NRRL), 1815 N. University Street, Peoria, Ill., 61604:

| Deposited Material | Date of Deposit | Accession Number |
|---|---|---|
| *E. coli*/pRS160 | January 21, 1994 | NRRL B-21175 |
| *E. coli*/pRS161 | January 21, 1994 | NRRL B-21176 |

We claim:

1. An isolated nucleic acid encoding a human metabotropic glutamate receptor which comprises the amino acid sequence of SEQ ID NO:2.

2. An isolated nucleic acid as claimed in claim 1, wherein said nucleic acid is selected from the group consisting of:
   (a) SEQ ID NO:1;
   (b) SEQ ID NO:3; and
   (c) a nucleic acid comprising a sequence of 18 or more contiguous bases from SEQ ID NO:1 or SEQ ID NO:3.

3. A composition as claimed in claim 2 wherein the isolated nucleic acid is deoxyribonucleic acid.

4. A composition as claimed in claim 3 which is SEQ ID NO:1 or a sequence complementary to SEQ ID NO:1.

5. An expression vector capable of producing a human metabotropic glutamate receptor in a host cell which comprises a nucleic acid as claimed in claim 2 in combination with regulatory elements necessary for expression of the nucleic acid in the host cell.

6. An expression vector as claimed in claim 5 for use in a host cell wherein the host cell is *Escherichia coli*.

7. An expression vector as claimed in claim 5 for use in a host cell wherein the host cell is a mammalian cell line.

8. An expression vector as claimed in claim 7 which comprises the BK virus enhancer.

9. An expression vector as claimed in claim 8 which further comprises an adenovirus late promoter.

10. A transfected host cell harboring an expression ector as claimed in claim 5.

11. A transfected host cell as claimed in claim 10 which is *Escherichia coli*.

12. A transfected host cell as claimed in claim 10 which is a mammalian cell line.

13. A transfected host cell as claimed in claim 12 which is AV-12.

14. An isolated nucleic acid encoding a human metabotropic glutamate receptor which comprises the amino acid sequence of SEQ ID NO:5.

15. An isolated nucleic acid as claimed in claim 14, wherein said nucleic acid is selected from the group consisting of:
   (a) SEQ ID NO:4;
   (b) SEQ ID NO:6; and
   (c) a nucleic acid comprising a sequence of 18 or more contiguous bases from SEQ ID NO:4 or SEQ ID NO:6.

16. A composition as claimed in claim 15 wherein the isolated nucleic acid is deoxyribonucleic acid.

17. A composition as claimed in claim 16 which is SEQ ID NO:4 or a sequence complementary to SEQ ID NO:4.

18. A composition as claimed in claim 16 which is pRS161.

19. A composition as claimed in claim 14 wherein the isolated nucleic acid is ribonucleic acid.

20. A composition as claimed in claim 19 which is SEQ ID NO:6.

21. An expression vector capable of producing a human metabotropic glutamate receptor in a host cell which comprises a nucleic acid as claimed in claim 15 in combination with regulatory elements necessary for expression of the nucleic acid in the host cell.

22. An expression vector as claimed in claim 21 wherein the host cell is *Escherichia coli*.

23. An expression vector as claimed in claim 21 wherein the host cell is a mammalian cell line.

24. An expression vector as claimed in claim 21 which comprises the BK virus enhancer.

25. An expression vector as claimed in claim 24 which further comprises an adenovirus late promoter.

26. A transfected host cell harboring an expression vector as claimed in claim 21.

27. A transfected host cell as claimed in claim 26 which is *Escherichia coli*.

28. A transfected host cell as claimed in claim 26 which is a mammalian cell line.

29. A transfected host cell as claimed in claim 28 which is AV-12.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 4207 base pairs
      (B) TYPE: nucleic acid
      (C) STRANDEDNESS: single
      (D) TOPOLOGY: linear (ii) MOLECULE TYPE: cDNA -continued (ix) FEATURE:
    (A) NAME/KEY: CDS
    (B) LOCATION: 460..3999

(xi) SEQUENCE DESCRIPTION: SEQ ID NO:1:

```
GTGATACAGA CCAGTGAGAA GGCAGCTTCT CCTTTTCACC TTCTTCTCCA TTCGCTACAT        60

GGGATTTTAT TGTTCAGAGT TTCTCAGGAC AAAGCTAGAG CTAATTTGTG TCTCTAATCC       120

TGGGCACTGG CCATTTGAAG CAGCCAAAGG TGCATTGACC AGGACTACGT GCAGCCCTTC       180

CTCCAGTGGG ACATAAGCAG GGGTTTTCTG TGGAAGTCTT AGTTGCATGA CATTCTACTG       240

TCAGCTGTGG AGTGTTCAGG TTTAGAAGAT CATGACCACA TGGATCATCT AACTAAATGG       300

TACATGGGGA CAAAATGGTC CTTTAGAAAA TACATCTGAA TTGCTGGCTA ATTTCTTGAT       360

TTGCGACTCA ACGTAGGACA TCGCTTGTTC GTAGCTATCA GAACCCTCCT GAATTTTCCC       420

CACCATGCTA TCTTTATTGG CTTGAACTCC TTTCCTAAA ATG GTC CTT CTG TTG         474
                                            Met Val Leu Leu Leu
                                              1               5

ATC CTG TCA GTC TTA CTT TTG AAA GAA GAT GTC CGT GGG AGT GCA CAG         522
Ile Leu Ser Val Leu Leu Leu Lys Glu Asp Val Arg Gly Ser Ala Gln
             10                  15                  20

TCC AGT GAG AGG AGG GTG GTG GCT CAC ATG CCG GGT GAC ATC ATT ATT         570
Ser Ser Glu Arg Arg Val Val Ala His Met Pro Gly Asp Ile Ile Ile
         25                  30                  35

GGA GCT CTC TTT TCT GTT CAT CAC CAG CCT ACT GTG GAC AAA GTT CAT         618
Gly Ala Leu Phe Ser Val His His Gln Pro Thr Val Asp Lys Val His
     40                  45                  50

GAG AGG AAG TGT GGG GCG GTC CGT GAA CAG TAT GGC ATT CAG AGA GTG         666
Glu Arg Lys Cys Gly Ala Val Arg Glu Gln Tyr Gly Ile Gln Arg Val
 55                  60                  65

GAG GCC ATG CTG CAT ACC CTG GAA AGG ATC AAT TCA GAC CCC ACA CTC         714
Glu Ala Met Leu His Thr Leu Glu Arg Ile Asn Ser Asp Pro Thr Leu
         70                  75                  80                  85

TTG CCC AAC ATC ACA CTG GGC TGT GAG ATA AGG GAC TCC TGC TGG CAT         762
Leu Pro Asn Ile Thr Leu Gly Cys Glu Ile Arg Asp Ser Cys Trp His
             90                  95                 100

TCG GCT GTG GCC CTA GAG CAG AGC ATT GAG TTC ATA AGA GAT TCC CTC         810
Ser Ala Val Ala Leu Glu Gln Ser Ile Glu Phe Ile Arg Asp Ser Leu
                105                 110                 115

ATT TCT TCA GAA GAG GAA GAA GGC TTG GTA CGC TGT GTG GAT GGC TCC         858
Ile Ser Ser Glu Glu Glu Glu Gly Leu Val Arg Cys Val Asp Gly Ser
            120                 125                 130

TCC TCT TCC TTC CGC TCC AAG AAG CCC ATA GTA GGG GTC ATT GGG CCT         906
Ser Ser Ser Phe Arg Ser Lys Lys Pro Ile Val Gly Val Ile Gly Pro
    135                 140                 145

GGC TCC AGT TCT GTA GCC ATT CAG GTC CAG AAT TTG CTC CAG CTT TTC         954
Gly Ser Ser Ser Val Ala Ile Gln Val Gln Asn Leu Leu Gln Leu Phe
150                 155                 160                 165

AAC ATA CCT CAG ATT GCT TAC TCA GCA ACC AGC ATG GAT CTG AGT GAC        1002
Asn Ile Pro Gln Ile Ala Tyr Ser Ala Thr Ser Met Asp Leu Ser Asp
                170                 175                 180

AAG ACT CTG TTC AAA TAT TTC ATG AGG GTT GTG CCT TCA GAT GCT CAG        1050
Lys Thr Leu Phe Lys Tyr Phe Met Arg Val Val Pro Ser Asp Ala Gln
            185                 190                 195

CAG GCA AGG GCC ATG GTG GAC ATA GTG AAG AGG TAC AAC TGG ACC TAT        1098
Gln Ala Arg Ala Met Val Asp Ile Val Lys Arg Tyr Asn Trp Thr Tyr
        200                 205                 210

GTA TCA GCC GTG CAC ACA GAA GGC AAC TAT GGA GAA AGT GGG ATG GAA        1146
Val Ser Ala Val His Thr Glu Gly Asn Tyr Gly Glu Ser Gly Met Glu
```

```
          215                 220                 225
GCC TTC AAA GAT ATG TCA GCG AAG GAA GGG ATT TGC ATC GCC CAC TCT    1194
Ala Phe Lys Asp Met Ser Ala Lys Glu Gly Ile Cys Ile Ala His Ser
230             235                 240                 245

TAC AAA ATC TAC AGT AAT GCA GGG GAG CAG AGC TTT GAT AAG CTG CTG    1242
Tyr Lys Ile Tyr Ser Asn Ala Gly Glu Gln Ser Phe Asp Lys Leu Leu
                250                 255                 260

AAG AAG CTC ACA AGT CAC TTG CCC AAG GCC CGG GTG GTG GCC TGC TTC    1290
Lys Lys Leu Thr Ser His Leu Pro Lys Ala Arg Val Val Ala Cys Phe
                    265                 270                 275

TGT GAG GGC ATG ACG GTG AGA GGT CTG CTG ATG GCC ATG AGG CGC CTG    1338
Cys Glu Gly Met Thr Val Arg Gly Leu Leu Met Ala Met Arg Arg Leu
            280                 285                 290

GGT CTA GCG GGA GAA TTT CTG CTT CTG GGC AGT GAT GGC TGG GCT GAC    1386
Gly Leu Ala Gly Glu Phe Leu Leu Leu Gly Ser Asp Gly Trp Ala Asp
        295                 300                 305

AGG TAT GAT GTG ACA GAT GGA TAT CAG CGA GAA GCT GTT GGT GGC ATC    1434
Arg Tyr Asp Val Thr Asp Gly Tyr Gln Arg Glu Ala Val Gly Gly Ile
310             315                 320                 325

ACA ATC AAG CTC CAA TCT CCC GAT GTC AAG TGG TTT GAT GAT TAT TAT    1482
Thr Ile Lys Leu Gln Ser Pro Asp Val Lys Trp Phe Asp Asp Tyr Tyr
                330                 335                 340

CTG AAG CTC CGG CCA GAA ACA AAC CAC CGA AAC CCT TGG TTT CAA GAA    1530
Leu Lys Leu Arg Pro Glu Thr Asn His Arg Asn Pro Trp Phe Gln Glu
                    345                 350                 355

TTT TGG CAG CAT CGT TTT CAG TGC CGA CTG GAA GGG TTT CCA CAG GAG    1578
Phe Trp Gln His Arg Phe Gln Cys Arg Leu Glu Gly Phe Pro Gln Glu
            360                 365                 370

AAC AGC AAA TAC AAC AAG ACT TGC AAT AGT TCT CTG ACT CTG AAA ACA    1626
Asn Ser Lys Tyr Asn Lys Thr Cys Asn Ser Ser Leu Thr Leu Lys Thr
        375                 380                 385

CAT CAT GTT CAG GAT TCC AAA ATG GGA TTT GTG ATC AAC GCC ATC TAT    1674
His His Val Gln Asp Ser Lys Met Gly Phe Val Ile Asn Ala Ile Tyr
390                 395                 400                 405

TCG ATG GCC TAT GGG CTC CAC AAC ATG CAG ATG TCC CTC TGC CCA GGC    1722
Ser Met Ala Tyr Gly Leu His Asn Met Gln Met Ser Leu Cys Pro Gly
                410                 415                 420

TAT GCA GGA CTC TGT GAT GCC ATG AAG CCA ATT GAT GGA CGG AAA CTT    1770
Tyr Ala Gly Leu Cys Asp Ala Met Lys Pro Ile Asp Gly Arg Lys Leu
                    425                 430                 435

TTG GAG TCC CTG ATG AAA ACC AAT TTT ACT GGG GTT TCT GGA GAT ACG    1818
Leu Glu Ser Leu Met Lys Thr Asn Phe Thr Gly Val Ser Gly Asp Thr
            440                 445                 450

ATC CTA TTC GAT GAG AAT GGA GAC TCT CCA GGA AGG TAT GAA ATA ATG    1866
Ile Leu Phe Asp Glu Asn Gly Asp Ser Pro Gly Arg Tyr Glu Ile Met
        455                 460                 465

AAT TTC AAG GAA ATG GGA AAA GAT TAC TTT GAT TAT ATC AAC GTT GGA    1914
Asn Phe Lys Glu Met Gly Lys Asp Tyr Phe Asp Tyr Ile Asn Val Gly
470                 475                 480                 485

AGT TGG GAC AAT GGA GAA TTA AAA ATG GAT GAT GAT GAA GTA TGG TCC    1962
Ser Trp Asp Asn Gly Glu Leu Lys Met Asp Asp Asp Glu Val Trp Ser
                490                 495                 500

AAG AAA AGC AAC ATC ATC AGA TCT GTG TGC AGT GAA CCA TGT GAG AAA    2010
Lys Lys Ser Asn Ile Ile Arg Ser Val Cys Ser Glu Pro Cys Glu Lys
                    505                 510                 515

GGC CAG ATC AAG GTG ATC CGA AAG GGA GAA GTC AGC TGT TGT TGG ACC    2058
Gly Gln Ile Lys Val Ile Arg Lys Gly Glu Val Ser Cys Cys Trp Thr
            520                 525                 530

TGT ACA CCT TGT AAG GAG AAT GAG TAT GTC TTT GAT GAG TAC ACA TGC    2106
```

-continued

| | | |
|---|---|---|
| Cys Thr Pro Cys Lys Glu Asn Glu Tyr Val Phe Asp Glu Tyr Thr Cys<br>535 540 545 | | |
| AAG GCA TGC CAA CTG GGG TCT TGG CCC ACT GAT GAT CTC ACA GGT TGT<br>Lys Ala Cys Gln Leu Gly Ser Trp Pro Thr Asp Asp Leu Thr Gly Cys<br>550 555 560 565 | | 2154 |
| GAC TTG ATC CCA GTA CAG TAT CTT CGA TGG GGT GAC CCT GAA CCC ATT<br>Asp Leu Ile Pro Val Gln Tyr Leu Arg Trp Gly Asp Pro Glu Pro Ile<br>570 575 580 | | 2202 |
| GCA GCT GTG GTG TTT GCC TGC CTT GGC CTC CTG GCC ACC CTG TTT GTT<br>Ala Ala Val Val Phe Ala Cys Leu Gly Leu Leu Ala Thr Leu Phe Val<br>585 590 595 | | 2250 |
| ACT GTA GTC TTC ATC ATT TAC CGT GAT ACA CCA GTA GTC AAG TCC TCA<br>Thr Val Val Phe Ile Ile Tyr Arg Asp Thr Pro Val Val Lys Ser Ser<br>600 605 610 | | 2298 |
| AGC AGG GAA CTC TGC TAC ATT ATC CTT GCT GGC ATC TGC CTG GGC TAC<br>Ser Arg Glu Leu Cys Tyr Ile Ile Leu Ala Gly Ile Cys Leu Gly Tyr<br>615 620 625 | | 2346 |
| TTA TGT ACC TTC TGC CTC ATT GCG AAG CCC AAA CAG ATT TAC TGC TAC<br>Leu Cys Thr Phe Cys Leu Ile Ala Lys Pro Lys Gln Ile Tyr Cys Tyr<br>630 635 640 645 | | 2394 |
| CTT CAG AGA ATT GGC ATT GGT CTC TCC CCA GCC ATG AGC TAC TCA GCC<br>Leu Gln Arg Ile Gly Ile Gly Leu Ser Pro Ala Met Ser Tyr Ser Ala<br>650 655 660 | | 2442 |
| CTT GTA ACA AAG ACC AAC CGT ATT GCA AGG ATC CTG GCT GGC AGC AAG<br>Leu Val Thr Lys Thr Asn Arg Ile Ala Arg Ile Leu Ala Gly Ser Lys<br>665 670 675 | | 2490 |
| AAG AAG ATC TGT ACC AAA AAG CCC AGA TTC ATG AGT GCC TGT GCC CAG<br>Lys Lys Ile Cys Thr Lys Lys Pro Arg Phe Met Ser Ala Cys Ala Gln<br>680 685 690 | | 2538 |
| CTA GTG ATT GCT TTC ATT CTC ATA TGC ATC CAG TTG GGC ATC ATC GTT<br>Leu Val Ile Ala Phe Ile Leu Ile Cys Ile Gln Leu Gly Ile Ile Val<br>695 700 705 | | 2586 |
| GCC CTC TTT ATA ATG GAG CCT CCT GAC ATA ATG CAT GAC TAC CCA AGC<br>Ala Leu Phe Ile Met Glu Pro Pro Asp Ile Met His Asp Tyr Pro Ser<br>710 715 720 725 | | 2634 |
| ATT CGA GAA GTC TAC CTG ATC TGT AAC ACC ACC AAC CTA GGA GTT GTC<br>Ile Arg Glu Val Tyr Leu Ile Cys Asn Thr Thr Asn Leu Gly Val Val<br>730 735 740 | | 2682 |
| ACT CCA CTT GGA TAC AAT GGA TTG TTG ATT TTG AGC TGC ACC TTC TAT<br>Thr Pro Leu Gly Tyr Asn Gly Leu Leu Ile Leu Ser Cys Thr Phe Tyr<br>745 750 755 | | 2730 |
| GCG TTC AAG ACC AGA AAT GTT CCA GCT AAC TTC AAC GAG GCC AAG TAT<br>Ala Phe Lys Thr Arg Asn Val Pro Ala Asn Phe Asn Glu Ala Lys Tyr<br>760 765 770 | | 2778 |
| ATC GCC TTC ACA ATG TAC ACG ACC TGC ATT ATA TGG CTA GCT TTT GTG<br>Ile Ala Phe Thr Met Tyr Thr Thr Cys Ile Ile Trp Leu Ala Phe Val<br>775 780 785 | | 2826 |
| CCA ATC TAC TTT GGC AGC AAC TAC AAA ATC ATC ACC ATG TGT TTC TCG<br>Pro Ile Tyr Phe Gly Ser Asn Tyr Lys Ile Ile Thr Met Cys Phe Ser<br>790 795 800 805 | | 2874 |
| GTC AGC CTC AGT GCC ACA GTG GCC CTA GGC TGC ATG TTT GTG CCG AAG<br>Val Ser Leu Ser Ala Thr Val Ala Leu Gly Cys Met Phe Val Pro Lys<br>810 815 820 | | 2922 |
| GTG TAC ATC ATC CTG GCC AAA CCA GAG AGA AAC GTG CGC AGC GCC TTC<br>Val Tyr Ile Ile Leu Ala Lys Pro Glu Arg Asn Val Arg Ser Ala Phe<br>825 830 835 | | 2970 |
| ACC ACA TCT ACC GTG GTG CGC ATG CAT GTA GGG GAT GGC AAG TCA TCC<br>Thr Thr Ser Thr Val Val Arg Met His Val Gly Asp Gly Lys Ser Ser<br>840 845 850 | | 3018 |

```
TCC GCA GCC AGC AGA TCC AGC AGC CTA GTC AAC CTG TGG AAG AGA AGG         3066
Ser Ala Ala Ser Arg Ser Ser Ser Leu Val Asn Leu Trp Lys Arg Arg
    855                 860                 865

GGC TCC TCT GGG GAA ACC TTA AGT TCC AAT GGA AAA TCC GTC ACG TGG         3114
Gly Ser Ser Gly Glu Thr Leu Ser Ser Asn Gly Lys Ser Val Thr Trp
870                 875                 880                 885

GCC CAG AAT GAG AAG AGC AGC CGG GGG CAG CAC CTG TGG CAG CGC CTG         3162
Ala Gln Asn Glu Lys Ser Ser Arg Gly Gln His Leu Trp Gln Arg Leu
            890                 895                 900

TCC ATC CAC ATC AAC AAG AAA GAA AAC CCC AAC CAA ACG GCC GTC ATC         3210
Ser Ile His Ile Asn Lys Lys Glu Asn Pro Asn Gln Thr Ala Val Ile
                905                 910                 915

AAG CCC TTC CCC AAG AGC ACG GAG AGC CGT GGC CTG GGC GCT GGC GCT         3258
Lys Pro Phe Pro Lys Ser Thr Glu Ser Arg Gly Leu Gly Ala Gly Ala
        920                 925                 930

GGC GCA GGC GGG AGC GCT GGG GGC GTG GGG GCC ACG GGC GGT GCG GGC         3306
Gly Ala Gly Gly Ser Ala Gly Gly Val Gly Ala Thr Gly Gly Ala Gly
    935                 940                 945

TGC GCA GGC GCC GGC CCA GGC GGG CCC GAG TCC CCA GAC GCC GGC CCC         3354
Cys Ala Gly Ala Gly Pro Gly Gly Pro Glu Ser Pro Asp Ala Gly Pro
950                 955                 960                 965

AAG GCG CTG TAT GAT GTG GCC GAG GCT GAG GAG CAC TTC CCG GCG CCC         3402
Lys Ala Leu Tyr Asp Val Ala Glu Ala Glu Glu His Phe Pro Ala Pro
            970                 975                 980

GCG CGG CCG CGC TCA CCG TCG CCC ATC AGC ACG CTG AGC CAC CGC GCG         3450
Ala Arg Pro Arg Ser Pro Ser Pro Ile Ser Thr Leu Ser His Arg Ala
                985                 990                 995

GGC TCG GCC AGC CGC ACG GAC GAC GAT GTG CCG TCG CTG CAC TCG GAG         3498
Gly Ser Ala Ser Arg Thr Asp Asp Asp Val Pro Ser Leu His Ser Glu
        1000                1005                1010

CCT GTG GCG CGC AGC AGC TCC TCG CAG GGC TCC CTC ATG GAG CAG ATC         3546
Pro Val Ala Arg Ser Ser Ser Ser Gln Gly Ser Leu Met Glu Gln Ile
    1015                1020                1025

AGC AGT GTG GTC ACC CGC TTC ACG GCC AAC ATC AGC GAG CTC AAC TCC         3594
Ser Ser Val Val Thr Arg Phe Thr Ala Asn Ile Ser Glu Leu Asn Ser
1030                1035                1040                1045

ATG ATG CTG TCC ACC GCG GCC CCC AGC CCC GGC GTC GGC GCC CCG CTC         3642
Met Met Leu Ser Thr Ala Ala Pro Ser Pro Gly Val Gly Ala Pro Leu
            1050                1055                1060

TGC TCG TCC TAC CTG ATC CCC AAA GAG ATC CAG TTG CCC ACG ACC ATG         3690
Cys Ser Ser Tyr Leu Ile Pro Lys Glu Ile Gln Leu Pro Thr Thr Met
                1065                1070                1075

ACG ACC TTT GCC GAA ATC CAG CCT CTG CCG GCC ATC GAA GTC ACG GGC         3738
Thr Thr Phe Ala Glu Ile Gln Pro Leu Pro Ala Ile Glu Val Thr Gly
        1080                1085                1090

GGC GCG CAG CCC GCG GCA GGG GCG CAG GCG GCT GGG GAC GCG GCC CGG         3786
Gly Ala Gln Pro Ala Ala Gly Ala Gln Ala Ala Gly Asp Ala Ala Arg
    1095                1100                1105

GAG AGC CCC GCG GCC GGT CCC GAG GCT GCG GCC GCC AAG CCA GAC CTG         3834
Glu Ser Pro Ala Ala Gly Pro Glu Ala Ala Ala Ala Lys Pro Asp Leu
1110                1115                1120                1125

GAG GAG CTG GTG GCT CTC ACC CCG CCG TCC CCC TTC AGA GAC TCG GTG         3882
Glu Glu Leu Val Ala Leu Thr Pro Pro Ser Pro Phe Arg Asp Ser Val
            1130                1135                1140

GAC TCG GGG AGC ACA ACC CCC AAC TCG CCA GTG TCC GAG TCG GCC CTC         3930
Asp Ser Gly Ser Thr Thr Pro Asn Ser Pro Val Ser Glu Ser Ala Leu
                1145                1150                1155

TGT ATC CCG TCG TCT CCC AAA TAT GAC ACT CTT ATC ATA AGA GAT TAC         3978
Cys Ile Pro Ser Ser Pro Lys Tyr Asp Thr Leu Ile Ile Arg Asp Tyr
        1160                1165                1170
```

```
ACT CAG AGC TCC TCG CCG CTG TGAATGTCCC TGGAAAGCAC GCCGGCCTGC      4029
Thr Gln Ser Ser Ser Pro Leu
    1175                1180

GCGTGCGGAG CGGAGCCCCC CGTGTTCACA CACACACAAT GGCAAGCATA GCCGCCTGGT  4089

TACGGCCCAG GGGGAAGGTG CCAAGGGCAC CCCTTTATGG AAACACGAGA TCAGTAGCGC  4149

TATCTCATGA CAACCCACGA AGAAACCGAC GACAAATCTC GCGGCAGATT TTCTTCTA    4207

(2) INFORMATION FOR SEQ ID NO:2:

(i) SEQUENCE CHARACTERISTICS:
         (A) LENGTH: 1180 amino acids
         (B) TYPE: amino acid
         (D) TOPOLOGY: linear (ii) MOLECULE TYPE: protein (xi) SEQUENCE DESCRIPTION: SEQ ID NO:2:

Met Val Leu Leu Ile Leu Ser Val Leu Leu Lys Glu Asp Val
 1               5                  10                  15

Arg Gly Ser Ala Gln Ser Ser Glu Arg Arg Val Ala His Met Pro
             20                  25                  30

Gly Asp Ile Ile Ile Gly Ala Leu Phe Ser Val His His Gln Pro Thr
             35                  40                  45

Val Asp Lys Val His Glu Arg Lys Cys Gly Ala Val Arg Glu Gln Tyr
     50                  55                  60

Gly Ile Gln Arg Val Glu Ala Met Leu His Thr Leu Glu Arg Ile Asn
 65                  70                  75                  80

Ser Asp Pro Thr Leu Leu Pro Asn Ile Thr Leu Gly Cys Glu Ile Arg
                 85                  90                  95

Asp Ser Cys Trp His Ser Ala Val Ala Leu Glu Gln Ser Ile Glu Phe
             100                 105                 110

Ile Arg Asp Ser Leu Ile Ser Ser Glu Glu Glu Gly Leu Val Arg
             115                 120                 125

Cys Val Asp Gly Ser Ser Ser Phe Arg Ser Lys Lys Pro Ile Val
         130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                 165                 170                 175

Met Asp Leu Ser Asp Lys Thr Leu Phe Lys Tyr Phe Met Arg Val Val
             180                 185                 190

Pro Ser Asp Ala Gln Gln Ala Arg Ala Met Val Asp Ile Val Lys Arg
         195                 200                 205

Tyr Asn Trp Thr Tyr Val Ser Ala Val His Thr Glu Gly Asn Tyr Gly
     210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                 245                 250                 255

Phe Asp Lys Leu Leu Lys Lys Leu Thr Ser His Leu Pro Lys Ala Arg
             260                 265                 270

Val Val Ala Cys Phe Cys Glu Gly Met Thr Val Arg Gly Leu Leu Met
         275                 280                 285

Ala Met Arg Arg Leu Gly Leu Ala Gly Glu Phe Leu Leu Leu Gly Ser
     290                 295                 300
```

```
Asp Gly Trp Ala Asp Arg Tyr Asp Val Thr Asp Gly Tyr Gln Arg Glu
305                 310                 315                 320
Ala Val Gly Gly Ile Thr Ile Lys Leu Gln Ser Pro Asp Val Lys Trp
                325                 330                 335
Phe Asp Asp Tyr Tyr Leu Lys Leu Arg Pro Glu Thr Asn His Arg Asn
                340                 345                 350
Pro Trp Phe Gln Glu Phe Trp Gln His Arg Phe Gln Cys Arg Leu Glu
                355                 360                 365
Gly Phe Pro Gln Glu Asn Ser Lys Tyr Asn Lys Thr Cys Asn Ser Ser
                370                 375                 380
Leu Thr Leu Lys Thr His His Val Gln Asp Ser Lys Met Gly Phe Val
385                 390                 395                 400
Ile Asn Ala Ile Tyr Ser Met Ala Tyr Gly Leu His Asn Met Gln Met
                405                 410                 415
Ser Leu Cys Pro Gly Tyr Ala Gly Leu Cys Asp Ala Met Lys Pro Ile
                420                 425                 430
Asp Gly Arg Lys Leu Leu Glu Ser Leu Met Lys Thr Asn Phe Thr Gly
                435                 440                 445
Val Ser Gly Asp Thr Ile Leu Phe Asp Glu Asn Gly Asp Ser Pro Gly
450                 455                 460
Arg Tyr Glu Ile Met Asn Phe Lys Glu Met Gly Lys Asp Tyr Phe Asp
465                 470                 475                 480
Tyr Ile Asn Val Gly Ser Trp Asp Asn Gly Glu Leu Lys Met Asp Asp
                485                 490                 495
Asp Glu Val Trp Ser Lys Lys Ser Asn Ile Ile Arg Ser Val Cys Ser
                500                 505                 510
Glu Pro Cys Glu Lys Gly Gln Ile Lys Val Ile Arg Lys Gly Glu Val
                515                 520                 525
Ser Cys Cys Trp Thr Cys Thr Pro Cys Lys Glu Asn Glu Tyr Val Phe
                530                 535                 540
Asp Glu Tyr Thr Cys Lys Ala Cys Gln Leu Gly Ser Trp Pro Thr Asp
545                 550                 555                 560
Asp Leu Thr Gly Cys Asp Leu Ile Pro Val Gln Tyr Leu Arg Trp Gly
                565                 570                 575
Asp Pro Glu Pro Ile Ala Ala Val Val Phe Ala Cys Leu Gly Leu Leu
                580                 585                 590
Ala Thr Leu Phe Val Thr Val Val Phe Ile Ile Tyr Arg Asp Thr Pro
                595                 600                 605
Val Val Lys Ser Ser Ser Arg Glu Leu Cys Tyr Ile Ile Leu Ala Gly
610                 615                 620
Ile Cys Leu Gly Tyr Leu Cys Thr Phe Cys Leu Ile Ala Lys Pro Lys
625                 630                 635                 640
Gln Ile Tyr Cys Tyr Leu Gln Arg Ile Gly Ile Gly Leu Ser Pro Ala
                645                 650                 655
Met Ser Tyr Ser Ala Leu Val Thr Lys Thr Asn Arg Ile Ala Arg Ile
                660                 665                 670
Leu Ala Gly Ser Lys Lys Lys Ile Cys Thr Lys Lys Pro Arg Phe Met
                675                 680                 685
Ser Ala Cys Ala Gln Leu Val Ile Ala Phe Ile Leu Ile Cys Ile Gln
                690                 695                 700
Leu Gly Ile Ile Val Ala Leu Phe Ile Met Glu Pro Pro Asp Ile Met
705                 710                 715                 720
```

```
His Asp Tyr Pro Ser Ile Arg Glu Val Tyr Leu Ile Cys Asn Thr Thr
            725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
            755                 760                 765

Asn Glu Ala Lys Tyr Ile Ala Phe Thr Met Tyr Thr Thr Cys Ile Ile
770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Lys Val Tyr Ile Ile Leu Ala Lys Pro Glu Arg Asn
            820                 825                 830

Val Arg Ser Ala Phe Thr Thr Ser Thr Val Val Arg Met His Val Gly
            835                 840                 845

Asp Gly Lys Ser Ser Ser Ala Ala Ser Arg Ser Ser Ser Leu Val Asn
850                 855                 860

Leu Trp Lys Arg Arg Gly Ser Ser Gly Glu Thr Leu Ser Ser Asn Gly
865                 870                 875                 880

Lys Ser Val Thr Trp Ala Gln Asn Glu Lys Ser Ser Arg Gly Gln His
                885                 890                 895

Leu Trp Gln Arg Leu Ser Ile His Ile Asn Lys Lys Glu Asn Pro Asn
            900                 905                 910

Gln Thr Ala Val Ile Lys Pro Phe Pro Lys Ser Thr Glu Ser Arg Gly
            915                 920                 925

Leu Gly Ala Gly Ala Gly Gly Ser Ala Gly Gly Val Gly Ala
            930                 935                 940

Thr Gly Gly Ala Gly Cys Ala Gly Ala Gly Pro Gly Gly Pro Glu Ser
945                 950                 955                 960

Pro Asp Ala Gly Pro Lys Ala Leu Tyr Asp Val Ala Glu Ala Glu Glu
                965                 970                 975

His Phe Pro Ala Pro Ala Arg Pro Arg Ser Pro Ser Pro Ile Ser Thr
            980                 985                 990

Leu Ser His Arg Ala Gly Ser Ala Ser Arg Thr Asp Asp Val Pro
            995                 1000                1005

Ser Leu His Ser Glu Pro Val Ala Arg Ser Ser Ser Gln Gly Ser
            1010                1015                1020

Leu Met Glu Gln Ile Ser Ser Val Val Thr Arg Phe Thr Ala Asn Ile
1025                1030                1035                1040

Ser Glu Leu Asn Ser Met Met Leu Ser Thr Ala Ala Pro Ser Pro Gly
            1045                1050                1055

Val Gly Ala Pro Leu Cys Ser Ser Tyr Leu Ile Pro Lys Glu Ile Gln
            1060                1065                1070

Leu Pro Thr Thr Met Thr Thr Phe Ala Glu Ile Gln Pro Leu Pro Ala
            1075                1080                1085

Ile Glu Val Thr Gly Gly Ala Gln Pro Ala Gly Ala Gln Ala Ala
            1090                1095                1100

Gly Asp Ala Ala Arg Glu Ser Pro Ala Gly Pro Glu Ala Ala Ala
1105                1110                1115                1120

Ala Lys Pro Asp Leu Glu Glu Leu Val Ala Leu Thr Pro Pro Ser Pro
            1125                1130                1135

Phe Arg Asp Ser Val Asp Ser Gly Ser Thr Thr Pro Asn Ser Pro Val
```

```
              1140              1145              1150
Ser Glu Ser Ala Leu Cys Ile Pro Ser Ser Pro Lys Tyr Asp Thr Leu
              1155              1160              1165

Ile Ile Arg Asp Tyr Thr Gln Ser Ser Pro Leu
              1170              1175          1180
```

(2) INFORMATION FOR SEQ ID NO:3:

(i) SEQUENCE CHARACTERISTICS:
        (A) LENGTH: 4207 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

```
GUGAUACAGA CCAGUGAGAA GGCAGCUUCU CCUUUUCACC UUCUUUCUCCA UUCGCUACAU      60

GGGAUUUUAU UGUUCAGAGU UUCUCAGGAC AAAGCUAGAG CUAAUUUGUG UCUCUAAUCC     120

UGGGCACUGG CCAUUUGAAG CAGCCAAAGG UGCAUUGACC AGGACUACGU GCAGCCCUUC     180

CUCCAGUGGG ACAUAAGCAG GGGUUUUCUG UGGAAGUCUU AGUUGCAUGA CAUUCUACUG     240

UCAGCUGUGG AGUGUUCAGG UUUAGAAGAU CAUGACCACA UGGAUCAUCU AACUAAAUGG     300

UACAUGGGGA CAAAAUGGUC CUUUAGAAAA UACAUCUGAA UUGCUGGCUA AUUUCUUGAU     360

UUGCGACUCA ACGUAGGACA UCGCUUGUUC GUAGCUAUCA GAACCCUCCU GAAUUCUCCC     420

CACCUUGCUA UCUUUAUUGG CUUGAACUCC UUUCCUAAAA UGGUCCUUCU GUUGAUCCUG     480

UCAGUCUUAC UUUUGAAAGA AGAUGUCCGU GGGAGUGCAC AGUCCAGUGA GAGGAGGGUG     540

GUGGCUCACA UGCCGGGUGA CAUCAUUAUU GGAGCUCUCU UUUCUGUUCA UCACCAGCCU     600

ACUGGGACA AAGUUCAUGA GAGGAAGUGU GGGGCGGUCC GUGAACAGUA UGGCAUUCAG     660

AGAGUGGAGG CCAUGCUGCA UACCCUGGAA AGGAUCAAUU CAGACCCCAC ACUCUUGCCC     720

AACAUCACAC UGGGCUGUGA UAAGGGAC UCCUGCUGGC AUUCGGCUGU GGCCCUAGAG     780

CAGAGCAUUG AGUUCAUAAG AGAUUCCCUC AUUUCUUCAG AAGAGGAAGA AGGCUUGGUA     840

CGCUGUGUGG AUGGCUCCUC UCUCUUCCUUC CGCUCCAAGA AGCCCAUAGU AGGGGUCAUU     900

GGGCCUGGCU CCAGUUCUGU AGCCAUUCAG GUCCAGAAUU UGCUCCAGCU UUUCAACAUA     960

CCUCAGAUUG CUUACUCAGC AACCAGCAUG GAUCUGAGUG ACAAGACUCU GUUCAAAUAU    1020

UUCAUGAGGG UUGUGCCUUC AGAUGCUCAG CAGGCAAGGG CCAUGGUGGA CAUAGUGAAG    1080

AGGUACAACU GGACCUAUGU AUCAGCCGUG CACACAGAAG GCAACUAUGG AGAAAGUGGG    1140

AUGGAAGCCU UCAAAGAUAU GUCAGCGAAG GAAGGGAUUU GCAUCGCCCA CUCUUACAAA    1200

AUCUACAGUA AUGCAGGGGA GCAGAGCUUU GAUAAGCUGC UGAAGAAGCU CACAAGUCAC    1260

UUGCCCAAGG CCCGGGUGGU GGCCUGCUUC UGUGAGGGCA UGACGGUGAG AGGUCUGCUG    1320

AUGGCCAUGA GGCGCCUGGG UCUAGCGGGA GAAUUCUGC UUCUGGGCAG UGAUGGCUGG    1380

GCUGACAGGU AUGAUGUGAC AGAUGGAUAU CAGCGAGAAG CUGUUGGUGG CAUCACAAUC    1440

AAGCUCCAAU CUCCCGAUGU CAAGUGGUUU GAUGAUUAUU AUCUGAAGCU CCGGCCAGAA    1500

ACAAACCACC GAAACCCUUG GUUCAAGAA UUUGGCAGC AUCGUUUUCA GUGCCGACUG    1560

GAAGGGUUUC CACAGGAGAA CAGCAAAUAC AACAAGACUU GCAAUAGUUC UCUGACUCUG    1620

AAAACACAUC AUGUUCAGGA UUCCAAAAUG GGAUUUGUGA UCAACGCCAU CUAUUCGAUG    1680

GCCUAUGGGC UCCACAACAU GCAGAUGUCC CUCUGCCCAG GCUAUGCAGG ACUCUGUGAU    1740
```

-continued

```
GCCAUGAAGC CAAUUGAUGG ACGGAAACUU UUGGAGUCCC UGAUGAAAAC CAAUUUUACU  1800
GGGGUUUCUG GAGAUACGAU CCUAUUCGAU GAGAAUGGAG ACUCUCCAGG AAGGUAUGAA  1860
AUAAUGAAUU UCAAGGAAAU GGGAAAAGAU UACUUUGAUU AUAUCAACGU UGGAAGUUGG  1920
GACAAUGGAG AAUUAAAAAU GGAUGAUGAU GAAGUAUGGU CCAAGAAAAG CAACAUCAUC  1980
AGAUCUGUGU GCAGUGAACC AUGUGAGAAA GGCCAGAUCA AGGUGAUCCG AAAGGGAGAA  2040
GUCAGCUGUU GUUGGACCUG UACACCUUGU AAGGAGAAUG AGUAUGUCUU UGAUGAGUAC  2100
ACAUGCAAGG CAUGCCAACU GGGGUCUUGG CCCACUGAUG AUCUCACAGG UUGUGACUUG  2160
AUCCCAGUAC AGUAUCUUCG AUGGGGUGAC CCUGAACCCA UUGCAGCUGU GGUGUUUGCC  2220
UGCCUUGGCC UCCUGGCCAC CCUGUUUGUU ACUGUAGUCU UCAUCAUUUA CCGUGAUACA  2280
CCAGUAGUCA AGUCCUCAAG CAGGGAACUC UGCUACAUUA UCCUUGCUGG CAUCUGCCUG  2340
GGCUACUUAU GUACCUUCUG CCUCAUUGCG AAGCCCAAAC AGAUUUACUG CUACCUUCAG  2400
AGAAUUGGCA UUGGUCUCUC CCCAGCCAUG AGCUACUCAG CCCUUGUAAC AAAGACCAAC  2460
CGUAUUGCAA GGAUCCUGGC UGGCAGCAAG AAGAAGAUCU GUACCAAAAA GCCCAGAUUC  2520
AUGAGUGCCU GUGCCCAGCU AGUGAUUGCU UUCAUUCUCA UAUGCAUCCA GUUGGGCAUC  2580
AUCGUUGCCC UCUUUAUAAU GGAGCCUCCU GACAUAAUGC AUGACUACCC AAGCAUUCGA  2640
GAAGUCUACC UGAUCUGUAA CACCACCAAC CUAGGAGUUG UCACUCCACU UGGAUACAAU  2700
GGAUUGUUGA UUUUGAGCUG CACCUUCUAU GCGUUCAAGA CCAGAAAUGU UCCAGCUAAC  2760
UUCAACGAGG CCAAGUAUAU CGCCUUCACA AUGUACACGA CCUGCAUUAU AUGGCUAGCU  2820
UUUGUGCCAA UCUACUUUGG CAGCAACUAC AAAAUCAUCA CCAUGUGUUU CUCGGUCAGC  2880
CUCAGUGCCA CAGUGGCCCU AGGCUGCAUG UUUGUGCCGA AGGUGUACAU CAUCCUGGCC  2940
AAACCAGAGA GAAACGUGCG CAGCGCCUUC ACCACAUCUA CCGUGGUGCG CAUGCAUGUA  3000
GGGGAUGGCA AGUCAUCCUC CGCAGCCAGC AGAUCCAGCA GCCUAGUCAA CCUGUGGAAG  3060
AGAAGGGGCU CCUCUGGGGA AACCUUAAGU UCCAAUGGAA AAUCCGUCAC GUGGGCCCAG  3120
AAUGAGAAGA GCAGCCGGGG GCAGCACCUG UGGCAGCGCC UGUCCAUCCA CAUCAACAAG  3180
AAAGAAAACC CCAACCAAAC GGCCGUCAUC AAGCCCUUCC CCAAGAGCAC GGAGAGCCGU  3240
GGCCUGGGCG CUGGCGCUGG CGCAGGCGGG AGCGCUGGGG GCGUGGGGGC CACGGGCGGU  3300
GCGGGCUGCG CAGGCGCCGG CCCAGGCGGG CCCGAGUCCC CAGACGCCGG CCCCAAGGCG  3360
CUGUAUGAUG UGGCCGAGGC UGAGGAGCAC UUCCCGGCGC CCGCGCGGCC GCGCUCACCG  3420
UCGCCCAUCA GCACGCUGAG CCACCGCGCG GGCUCGGCCA GCCGCACGGA CGACGAUGUG  3480
CCGUCGCUGC ACUCGGAGCC UGUGGCGCGC AGCAGCUCCU CGCAGGGCUC CCUCAUGGAG  3540
CAGAUCAGCA GUGUGGUCAC CCGCUUCACG GCCAACAUCA GCGAGCUCAA CUCCAUGAUG  3600
CUGUCCACCG CGGCCCCCAG CCCCGGCGUC GGCGCCCCGC UCUGCUCGUC CUACCUGAUC  3660
CCCAAAGAGA UCCAGUUGCC CACGACCAUG ACGACCUUUG CCGAAAUCCA GCCUCUGCCG  3720
GCCAUCGAAG UCACGGGCGG CGCGCAGCCC GCGGCAGGGG CGCAGGCGGC UGGGGACGCG  3780
GCCCGGGAGA GCCCCGCGGC CGGUCCCGAG GCUGCGGCCG CCAAGCCAGA CCUGGAGGAG  3840
CUGGUGGCUC UCACCCCGCC GUCCCCCUUC AGAGACUCGG UGGACUCGGG GAGCACAACC  3900
CCCAACUCGC CAGUGUCCGA GUCGGCCCUC UGUAUCCCGU CGUCUCCCAA AUAUGACACU  3960
CUUAUCAUAA GAGAUUACAC UCAGAGCUCC UCGCCGCUGU GAAUGUCCCU GGAAAGCACG  4020
CCGGCCUGCG CGUGCGGAGC GGAGCCCCCC GUGUUCACAC ACACACAAUG GCAAGCAUAG  4080
CCGCCUGGUU ACGGCCCAGG GGGAAGGUGC CAAGGGCACC CCUUUAUGGA AACACGAGAU  4140
```

```
CAGUAGCGCU AUCUCAUGAC AACCCACGAA GAAACCGACG ACAAAUCUCG CGGCAGAUUU    4200

UCUUCUA                                                              4207

(2) INFORMATION FOR SEQ ID NO:4:

(i) SEQUENCE CHARACTERISTICS:
        (A) LENGTH: 4303 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 460..4095

(xi) SEQUENCE DESCRIPTION: SEQ ID NO:4:

GTGATACAGA CCAGTGAGAA GGCAGCTTCT CCTTTTCACC TTCTTCTCCA TTCGCTACAT      60

GGGATTTTAT TGTTCAGAGT TTCTCAGGAC AAAGCTAGAG CTAATTTGTG TCTCTAATCC     120

TGGGCACTGG CCATTTGAAG CAGCCAAAGG TGCATTGACC AGGACTACGT GCAGCCCTTC     180

CTCCAGTGGG ACATAAGCAG GGGTTTTCTG TGGAAGTCTT AGTTGCATGA CATTCTACTG     240

TCAGCTGTGG AGTGTTCAGG TTTAGAAGAT CATGACCACA TGGATCATCT AACTAAATGG     300

TACATGGGGA CAAAATGGTC CTTTAGAAAA TACATCTGAA TTGCTGGCTA ATTTCTTGAT     360

TTGCGACTCA ACGTAGGACA TCGCTTGTTC GTAGCTATCA GAACCCTCCT GAATTTTCCC     420

CACCATGCTA TCTTTATTGG CTTGAACTCC TTTCCTAAA ATG GTC CTT CTG TTG       474
                                            Met Val Leu Leu Leu
                                              1               5

ATC CTG TCA GTC TTA CTT TTG AAA GAA GAT GTC CGT GGG AGT GCA CAG      522
Ile Leu Ser Val Leu Leu Leu Lys Glu Asp Val Arg Gly Ser Ala Gln
             10                  15                  20

TCC AGT GAG AGG AGG GTG GTG GCT CAC ATG CCG GGT GAC ATC ATT ATT      570
Ser Ser Glu Arg Arg Val Val Ala His Met Pro Gly Asp Ile Ile Ile
         25                  30                  35

GGA GCT CTC TTT TCT GTT CAT CAC CAG CCT ACT GTG GAC AAA GTT CAT      618
Gly Ala Leu Phe Ser Val His His Gln Pro Thr Val Asp Lys Val His
     40                  45                  50

GAG AGG AAG TGT GGG GCG GTC CGT GAA CAG TAT GGC ATT CAG AGA GTG      666
Glu Arg Lys Cys Gly Ala Val Arg Glu Gln Tyr Gly Ile Gln Arg Val
 55                  60                  65

GAG GCC ATG CTG CAT ACC CTG GAA AGG ATC AAT TCA GAC CCC ACA CTC      714
Glu Ala Met Leu His Thr Leu Glu Arg Ile Asn Ser Asp Pro Thr Leu
 70                  75                  80                  85

TTG CCC AAC ATC ACA CTG GGC TGT GAG ATA AGG GAC TCC TGC TGG CAT      762
Leu Pro Asn Ile Thr Leu Gly Cys Glu Ile Arg Asp Ser Cys Trp His
             90                  95                 100

TCG GCT GTG GCC CTA GAG CAG AGC ATT GAG TTC ATA AGA GAT TCC CTC      810
Ser Ala Val Ala Leu Glu Gln Ser Ile Glu Phe Ile Arg Asp Ser Leu
        105                 110                 115

ATT TCT TCA GAA GAG GAA GAA GGC TTG GTA CGC TGT GTG GAT GGC TCC      858
Ile Ser Ser Glu Glu Glu Glu Gly Leu Val Arg Cys Val Asp Gly Ser
        120                 125                 130

TCC TCT TCC TTC CGC TCC AAG AAG CCC ATA GTA GGG GTC ATT GGG CCT      906
Ser Ser Ser Phe Arg Ser Lys Lys Pro Ile Val Gly Val Ile Gly Pro
135                 140                 145

GGC TCC AGT TCT GTA GCC ATT CAG GTC CAG AAT TTG CTC CAG CTT TTC      954
Gly Ser Ser Ser Val Ala Ile Gln Val Gln Asn Leu Leu Gln Leu Phe
150                 155                 160                 165
```

```
AAC ATA CCT CAG ATT GCT TAC TCA GCA ACC AGC ATG GAT CTG AGT GAC    1002
Asn Ile Pro Gln Ile Ala Tyr Ser Ala Thr Ser Met Asp Leu Ser Asp
            170                 175                 180

AAG ACT CTG TTC AAA TAT TTC ATG AGG GTT GTG CCT TCA GAT GCT CAG    1050
Lys Thr Leu Phe Lys Tyr Phe Met Arg Val Val Pro Ser Asp Ala Gln
                185                 190                 195

CAG GCA AGG GCC ATG GTG GAC ATA GTG AAG AGG TAC AAC TGG ACC TAT    1098
Gln Ala Arg Ala Met Val Asp Ile Val Lys Arg Tyr Asn Trp Thr Tyr
            200                 205                 210

GTA TCA GCC GTG CAC ACA GAA GGC AAC TAT GGA GAA AGT GGG ATG GAA    1146
Val Ser Ala Val His Thr Glu Gly Asn Tyr Gly Glu Ser Gly Met Glu
        215                 220                 225

GCC TTC AAA GAT ATG TCA GCG AAG GAA GGG ATT TGC ATC GCC CAC TCT    1194
Ala Phe Lys Asp Met Ser Ala Lys Glu Gly Ile Cys Ile Ala His Ser
230                 235                 240                 245

TAC AAA ATC TAC AGT AAT GCA GGG GAG CAG AGC TTT GAT AAG CTG CTG    1242
Tyr Lys Ile Tyr Ser Asn Ala Gly Glu Gln Ser Phe Asp Lys Leu Leu
                250                 255                 260

AAG AAG CTC ACA AGT CAC TTG CCC AAG GCC CGG GTG GTG GCC TGC TTC    1290
Lys Lys Leu Thr Ser His Leu Pro Lys Ala Arg Val Val Ala Cys Phe
            265                 270                 275

TGT GAG GGC ATG ACG GTG AGA GGT CTG CTG ATG GCC ATG AGG CGC CTG    1338
Cys Glu Gly Met Thr Val Arg Gly Leu Leu Met Ala Met Arg Arg Leu
        280                 285                 290

GGT CTA GCG GGA GAA TTT CTG CTT CTG GGC AGT GAT GGC TGG GCT GAC    1386
Gly Leu Ala Gly Glu Phe Leu Leu Leu Gly Ser Asp Gly Trp Ala Asp
    295                 300                 305

AGG TAT GAT GTG ACA GAT GGA TAT CAG CGA GAA GCT GTT GGT GGC ATC    1434
Arg Tyr Asp Val Thr Asp Gly Tyr Gln Arg Glu Ala Val Gly Gly Ile
310                 315                 320                 325

ACA ATC AAG CTC CAA TCT CCC GAT GTC AAG TGG TTT GAT GAT TAT TAT    1482
Thr Ile Lys Leu Gln Ser Pro Asp Val Lys Trp Phe Asp Asp Tyr Tyr
                330                 335                 340

CTG AAG CTC CGG CCA GAA ACA AAC CAC CGA AAC CCT TGG TTT CAA GAA    1530
Leu Lys Leu Arg Pro Glu Thr Asn His Arg Asn Pro Trp Phe Gln Glu
            345                 350                 355

TTT TGG CAG CAT CGT TTT CAG TGC CGA CTG GAA GGG TTT CCA CAG GAG    1578
Phe Trp Gln His Arg Phe Gln Cys Arg Leu Glu Gly Phe Pro Gln Glu
        360                 365                 370

AAC AGC AAA TAC AAC AAG ACT TGC AAT AGT TCT CTG ACT CTG AAA ACA    1626
Asn Ser Lys Tyr Asn Lys Thr Cys Asn Ser Ser Leu Thr Leu Lys Thr
    375                 380                 385

CAT CAT GTT CAG GAT TCC AAA ATG GGA TTT GTG ATC AAC GCC ATC TAT    1674
His His Val Gln Asp Ser Lys Met Gly Phe Val Ile Asn Ala Ile Tyr
390                 395                 400                 405

TCG ATG GCC TAT GGG CTC CAC AAC ATG CAG ATG TCC CTC TGC CCA GGC    1722
Ser Met Ala Tyr Gly Leu His Asn Met Gln Met Ser Leu Cys Pro Gly
                410                 415                 420

TAT GCA GGA CTC TGT GAT GCC ATG AAG CCA ATT GAT GGA CGG AAA CTT    1770
Tyr Ala Gly Leu Cys Asp Ala Met Lys Pro Ile Asp Gly Arg Lys Leu
            425                 430                 435

TTG GAG TCC CTG ATG AAA ACC AAT TTT ACT GGG GTT TCT GGA GAT ACG    1818
Leu Glu Ser Leu Met Lys Thr Asn Phe Thr Gly Val Ser Gly Asp Thr
        440                 445                 450

ATC CTA TTC GAT GAG AAT GGA GAC TCT CCA GGA AGG TAT GAA ATA ATG    1866
Ile Leu Phe Asp Glu Asn Gly Asp Ser Pro Gly Arg Tyr Glu Ile Met
    455                 460                 465

AAT TTC AAG GAA ATG GGA AAA GAT TAC TTT GAT TAT ATC AAC GTT GGA    1914
Asn Phe Lys Glu Met Gly Lys Asp Tyr Phe Asp Tyr Ile Asn Val Gly
```

```
                    470                475                480                485
AGT TGG GAC AAT GGA GAA TTA AAA ATG GAT GAT GAT GAA GTA TGG TCC              1962
Ser Trp Asp Asn Gly Glu Leu Lys Met Asp Asp Asp Glu Val Trp Ser
                490                495                500

AAG AAA AGC AAC ATC ATC AGA TCT GTG TGC AGT GAA CCA TGT GAG AAA              2010
Lys Lys Ser Asn Ile Ile Arg Ser Val Cys Ser Glu Pro Cys Glu Lys
                505                510                515

GGC CAG ATC AAG GTG ATC CGA AAG GGA GAA GTC AGC TGT TGT TGG ACC              2058
Gly Gln Ile Lys Val Ile Arg Lys Gly Glu Val Ser Cys Cys Trp Thr
            520                525                530

TGT ACA CCT TGT AAG GAG AAT GAG TAT GTC TTT GAT GAG TAC ACA TGC              2106
Cys Thr Pro Cys Lys Glu Asn Glu Tyr Val Phe Asp Glu Tyr Thr Cys
        535                540                545

AAG GCA TGC CAA CTG GGG TCT TGG CCC ACT GAT GAT CTC ACA GGT TGT              2154
Lys Ala Cys Gln Leu Gly Ser Trp Pro Thr Asp Asp Leu Thr Gly Cys
550                555                560                565

GAC TTG ATC CCA GTA CAG TAT CTT CGA TGG GGT GAC CCT GAA CCC ATT              2202
Asp Leu Ile Pro Val Gln Tyr Leu Arg Trp Gly Asp Pro Glu Pro Ile
            570                575                580

GCA GCT GTG GTG TTT GCC TGC CTT GGC CTC CTG GCC ACC CTG TTT GTT              2250
Ala Ala Val Val Phe Ala Cys Leu Gly Leu Leu Ala Thr Leu Phe Val
        585                590                595

ACT GTA GTC TTC ATC ATT TAC CGT GAT ACA CCA GTA GTC AAG TCC TCA              2298
Thr Val Val Phe Ile Ile Tyr Arg Asp Thr Pro Val Val Lys Ser Ser
    600                605                610

AGC AGG GAA CTC TGC TAC ATT ATC CTT GCT GGC ATC TGC CTG GGC TAC              2346
Ser Arg Glu Leu Cys Tyr Ile Ile Leu Ala Gly Ile Cys Leu Gly Tyr
615                620                625

TTA TGT ACC TTC TGC CTC ATT GCG AAG CCC AAA CAG ATT TAC TGC TAC              2394
Leu Cys Thr Phe Cys Leu Ile Ala Lys Pro Lys Gln Ile Tyr Cys Tyr
630                635                640                645

CTT CAG AGA ATT GGC ATT GGT CTC TCC CCA GCC ATG AGC TAC TCA GCC              2442
Leu Gln Arg Ile Gly Ile Gly Leu Ser Pro Ala Met Ser Tyr Ser Ala
            650                655                660

CTT GTA ACA AAG ACC AAC CGT ATT GCA AGG ATC CTG GCT GGC AGC AAG              2490
Leu Val Thr Lys Thr Asn Arg Ile Ala Arg Ile Leu Ala Gly Ser Lys
        665                670                675

AAG AAG ATC TGT ACC AAA AAG CCC AGA TTC ATG AGT GCC TGT GCC CAG              2538
Lys Lys Ile Cys Thr Lys Lys Pro Arg Phe Met Ser Ala Cys Ala Gln
    680                685                690

CTA GTG ATT GCT TTC ATT CTC ATA TGC ATC CAG TTG GGC ATC ATC GTT              2586
Leu Val Ile Ala Phe Ile Leu Ile Cys Ile Gln Leu Gly Ile Ile Val
    695                700                705

GCC CTC TTT ATA ATG GAG CCT CCT GAC ATA ATG CAT GAC TAC CCA AGC              2634
Ala Leu Phe Ile Met Glu Pro Pro Asp Ile Met His Asp Tyr Pro Ser
710                715                720                725

ATT CGA GAA GTC TAC CTG ATC TGT AAC ACC ACC AAC CTA GGA GTT GTC              2682
Ile Arg Glu Val Tyr Leu Ile Cys Asn Thr Thr Asn Leu Gly Val Val
            730                735                740

ACT CCA CTT GGA TAC AAT GGA TTG TTG ATT TTG AGC TGC ACC TTC TAT              2730
Thr Pro Leu Gly Tyr Asn Gly Leu Leu Ile Leu Ser Cys Thr Phe Tyr
        745                750                755

GCG TTC AAG ACC AGA AAT GTT CCA GCT AAC TTC AAC GAG GCC AAG TAT              2778
Ala Phe Lys Thr Arg Asn Val Pro Ala Asn Phe Asn Glu Ala Lys Tyr
        760                765                770

ATC GCC TTC ACA ATG TAC ACG ACC TGC ATT ATA TGG CTA GCT TTT GTG              2826
Ile Ala Phe Thr Met Tyr Thr Thr Cys Ile Ile Trp Leu Ala Phe Val
    775                780                785

CCA ATC TAC TTT GGC AGC AAC TAC AAA ATC ATC ACC ATG TGT TTC TCG              2874
```

```
                                                                      -continued Pro Ile Tyr Phe Gly Ser Asn Tyr Lys Ile Ile Thr Met Cys Phe Ser
790                 795                 800                 805

GTC AGC CTC AGT GCC ACA GTG GCC CTA GGC TGC ATG TTT GTG CCG AAG        2922
Val Ser Leu Ser Ala Thr Val Ala Leu Gly Cys Met Phe Val Pro Lys
                810                 815                 820

GTG TAC ATC ATC CTG GCC AAA CCA GAG AGA AAC GTG CGC AGC GCC TTC        2970
Val Tyr Ile Ile Leu Ala Lys Pro Glu Arg Asn Val Arg Ser Ala Phe
            825                 830                 835

ACC ACA TCT ACC GTG GTG CGC ATG CAT GTA GGG GAT GGC AAG TCA TCC        3018
Thr Thr Ser Thr Val Val Arg Met His Val Gly Asp Gly Lys Ser Ser
            840                 845                 850

TCC GCA GCC AGC AGA TCC AGC AGC CTA GTC AAC CTG TGG AAG AGA AGG        3066
Ser Ala Ala Ser Arg Ser Ser Ser Leu Val Asn Leu Trp Lys Arg Arg
            855                 860                 865

GGC TCC TCT GGG GAA ACC TTA AGG TAC AAA GAC AGG AGA CTG GCC CAG        3114
Gly Ser Ser Gly Glu Thr Leu Arg Tyr Lys Asp Arg Arg Leu Ala Gln
870                 875                 880                 885

CAC AAG TCG GAA ATA GAG TGT TTC ACC CCC AAA GGG AGT ATG GGG AAT        3162
His Lys Ser Glu Ile Glu Cys Phe Thr Pro Lys Gly Ser Met Gly Asn
                890                 895                 900

GGT GGG AGA GCA ACA ATG AGC AGT TCC AAT GGA AAA TCC GTC ACG TGG        3210
Gly Gly Arg Ala Thr Met Ser Ser Ser Asn Gly Lys Ser Val Thr Trp
            905                 910                 915

GCC CAG AAT GAG AAG AGC AGC CGG GGG CAG CAC CTG TGG CAG CGC CTG        3258
Ala Gln Asn Glu Lys Ser Ser Arg Gly Gln His Leu Trp Gln Arg Leu
            920                 925                 930

TCC ATC CAC ATC AAC AAG AAA GAA AAC CCC AAC CAA ACG GCC GTC ATC        3306
Ser Ile His Ile Asn Lys Lys Glu Asn Pro Asn Gln Thr Ala Val Ile
            935                 940                 945

AAG CCC TTC CCC AAG AGC ACG GAG AGC CGT GGC CTG GGC GCT GGC GCT        3354
Lys Pro Phe Pro Lys Ser Thr Glu Ser Arg Gly Leu Gly Ala Gly Ala
950                 955                 960                 965

GGC GCA GGC GGG AGC GCT GGG GGC GTG GGG GCC ACG GGC GGT GCG GGC        3402
Gly Ala Gly Gly Ser Ala Gly Gly Val Gly Ala Thr Gly Gly Ala Gly
                970                 975                 980

TGC GCA GGC GCC GGC CCA GGC GGG CCC GAG TCC CCA GAC GCC GGC CCC        3450
Cys Ala Gly Ala Gly Pro Gly Gly Pro Glu Ser Pro Asp Ala Gly Pro
            985                 990                 995

AAG GCG CTG TAT GAT GTG GCC GAG GCT GAG GAG CAC TTC CCG GCG CCC        3498
Lys Ala Leu Tyr Asp Val Ala Glu Ala Glu Glu His Phe Pro Ala Pro
            1000                1005                1010

GCG CGG CCG CGC TCA CCG TCG CCC ATC AGC ACG CTG AGC CAC CGC GCG        3546
Ala Arg Pro Arg Ser Pro Ser Pro Ile Ser Thr Leu Ser His Arg Ala
            1015                1020                1025

GGC TCG GCC AGC CGC ACG GAC GAC GAT GTG CCG TCG CTG CAC TCG GAG        3594
Gly Ser Ala Ser Arg Thr Asp Asp Asp Val Pro Ser Leu His Ser Glu
1030                1035                1040                1045

CCT GTG GCG CGC AGC AGC TCC TCG CAG GGC TCC CTC ATG GAG CAG ATC        3642
Pro Val Ala Arg Ser Ser Ser Ser Gln Gly Ser Leu Met Glu Gln Ile
                1050                1055                1060

AGC AGT GTG GTC ACC CGC TTC ACG GCC AAC ATC AGC GAG CTC AAC TCC        3690
Ser Ser Val Val Thr Arg Phe Thr Ala Asn Ile Ser Glu Leu Asn Ser
            1065                1070                1075

ATG ATG CTG TCC ACC GCG GCC CCC AGC CCC GGC GTC GGC GCC CCG CTC        3738
Met Met Leu Ser Thr Ala Ala Pro Ser Pro Gly Val Gly Ala Pro Leu
            1080                1085                1090

TGC TCG TCC TAC CTG ATC CCC AAA GAG ATC CAG TTG CCC ACG ACC ATG        3786
Cys Ser Ser Tyr Leu Ile Pro Lys Glu Ile Gln Leu Pro Thr Thr Met
            1095                1100                1105
```

-continued

```
ACG ACC TTT GCC GAA ATC CAG CCT CTG CCG GCC ATC GAA GTC ACG GGC        3834
Thr Thr Phe Ala Glu Ile Gln Pro Leu Pro Ala Ile Glu Val Thr Gly
1110                1115                1120                1125

GGC GCG CAG CCC GCG GCA GGG GCG CAG GCG GCT GGG GAC GCG GCC CGG        3882
Gly Ala Gln Pro Ala Ala Gly Ala Gln Ala Ala Gly Asp Ala Ala Arg
                1130                1135                1140

GAG AGC CCC GCG GCC GGT CCC GAG GCT GCG GCC GCC AAG CCA GAC CTG        3930
Glu Ser Pro Ala Ala Gly Pro Glu Ala Ala Ala Lys Pro Asp Leu
            1145                1150                1155

GAG GAG CTG GTG GCT CTC ACC CCG CCG TCC CCC TTC AGA GAC TCG GTG        3978
Glu Glu Leu Val Ala Leu Thr Pro Pro Ser Pro Phe Arg Asp Ser Val
        1160                1165                1170

GAC TCG GGG AGC ACA ACC CCC AAC TCG CCA GTG TCC GAG TCG GCC CTC        4026
Asp Ser Gly Ser Thr Thr Pro Asn Ser Pro Val Ser Glu Ser Ala Leu
    1175                1180                1185

TGT ATC CCG TCG TCT CCC AAA TAT GAC ACT CTT ATC ATA AGA GAT TAC        4074
Cys Ile Pro Ser Ser Pro Lys Tyr Asp Thr Leu Ile Ile Arg Asp Tyr
1190                1195                1200                1205

ACT CAG AGC TCC TCG CCG CTG TGAATGTCCC TGGAAAGCAC GCCGGCCTGC            4125
Thr Gln Ser Ser Ser Pro Leu
                1210

GCGTGCGGAG CGGAGCCCCC CGTGTTCACA CACACACAAT GGCAAGCATA GCCGCCTGGT       4185

TACGGCCCAG GGGGAAGGTG CCAAGGGCAC CCCTTTATGG AAACACGAGA TCAGTAGCGC       4245

TATCTCATGA CAACCCACGA AGAAACCGAC GACAAATCTC GCGGCAGATT TTCTTCTA        4303

(2) INFORMATION FOR SEQ ID NO:5:

(i) SEQUENCE CHARACTERISTICS:
        (A) LENGTH: 1212 amino acids
        (B) TYPE: amino acid
        (D) TOPOLOGY: linear (ii) MOLECULE TYPE: protein (xi) SEQUENCE DESCRIPTION: SEQ ID NO:5:

Met Val Leu Leu Leu Ile Leu Ser Val Leu Leu Lys Glu Asp Val
  1               5                  10                  15

Arg Gly Ser Ala Gln Ser Ser Glu Arg Arg Val Val Ala His Met Pro
                20                  25                  30

Gly Asp Ile Ile Ile Gly Ala Leu Phe Ser Val His His Gln Pro Thr
            35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
                100                 105                 110

Ile Arg Asp Ser Leu Ile Ser Ser Glu Glu Glu Gly Leu Val Arg
            115                 120                 125

Cys Val Asp Gly Ser Ser Ser Phe Arg Ser Lys Lys Pro Ile Val
        130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175
```

-continued

Met Asp Leu Ser Asp Lys Thr Leu Phe Lys Tyr Phe Met Arg Val Val
              180                 185                 190

Pro Ser Asp Ala Gln Gln Ala Arg Ala Met Val Asp Ile Val Lys Arg
              195                 200                 205

Tyr Asn Trp Thr Tyr Val Ser Ala Val His Thr Glu Gly Asn Tyr Gly
              210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
              245                 250                 255

Phe Asp Lys Leu Leu Lys Lys Leu Thr Ser His Leu Pro Lys Ala Arg
              260                 265                 270

Val Val Ala Cys Phe Cys Glu Gly Met Thr Val Arg Gly Leu Leu Met
              275                 280                 285

Ala Met Arg Arg Leu Gly Leu Ala Gly Glu Phe Leu Leu Leu Gly Ser
              290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                  325                 330                 335

Phe Asp Asp Tyr Tyr Leu Lys Leu Arg Pro Glu Thr Asn His Arg Asn
              340                 345                 350

Pro Trp Phe Gln Glu Phe Trp Gln His Arg Phe Gln Cys Arg Leu Glu
              355                 360                 365

Gly Phe Pro Gln Glu Asn Ser Lys Tyr Asn Lys Thr Cys Asn Ser Ser
              370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                  405                 410                 415

Ser Leu Cys Pro Gly Tyr Ala Gly Leu Cys Asp Ala Met Lys Pro Ile
              420                 425                 430

Asp Gly Arg Lys Leu Leu Glu Ser Leu Met Lys Thr Asn Phe Thr Gly
              435                 440                 445

Val Ser Gly Asp Thr Ile Leu Phe Asp Glu Asn Gly Asp Ser Pro Gly
              450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                  485                 490                 495

Asp Glu Val Trp Ser Lys Lys Ser Asn Ile Ile Arg Ser Val Cys Ser
              500                 505                 510

Glu Pro Cys Glu Lys Gly Gln Ile Lys Val Ile Arg Lys Gly Glu Val
              515                 520                 525

Ser Cys Cys Trp Thr Cys Thr Pro Cys Lys Glu Asn Glu Tyr Val Phe
              530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
              565                 570                 575

Asp Pro Glu Pro Ile Ala Ala Val Val Phe Ala Cys Leu Gly Leu Leu
              580                 585                 590

Ala Thr Leu Phe Val Thr Val Val Phe Ile Ile Tyr Arg Asp Thr Pro

-continued

```
                595                 600                 605
Val Val Lys Ser Ser Arg Glu Leu Cys Tyr Ile Ile Leu Ala Gly
        610                 615                 620
Ile Cys Leu Gly Tyr Leu Cys Thr Phe Cys Leu Ile Ala Lys Pro Lys
625                 630                 635                 640
Gln Ile Tyr Cys Tyr Leu Gln Arg Ile Gly Ile Gly Leu Ser Pro Ala
                645                 650                 655
Met Ser Tyr Ser Ala Leu Val Thr Lys Thr Asn Arg Ile Ala Arg Ile
        660                 665                 670
Leu Ala Gly Ser Lys Lys Ile Cys Thr Lys Lys Pro Arg Phe Met
        675                 680                 685
Ser Ala Cys Ala Gln Leu Val Ile Ala Phe Ile Leu Ile Cys Ile Gln
        690                 695                 700
Leu Gly Ile Ile Val Ala Leu Phe Ile Met Glu Pro Pro Asp Ile Met
705                 710                 715                 720
His Asp Tyr Pro Ser Ile Arg Glu Val Tyr Leu Ile Cys Asn Thr Thr
                725                 730                 735
Asn Leu Gly Val Val Thr Pro Leu Gly Tyr Asn Gly Leu Leu Ile Leu
        740                 745                 750
Ser Cys Thr Phe Tyr Ala Phe Lys Thr Arg Asn Val Pro Ala Asn Phe
        755                 760                 765
Asn Glu Ala Lys Tyr Ile Ala Phe Thr Met Tyr Thr Thr Cys Ile Ile
        770                 775                 780
Trp Leu Ala Phe Val Pro Ile Tyr Phe Gly Ser Asn Tyr Lys Ile Ile
785                 790                 795                 800
Thr Met Cys Phe Ser Val Ser Leu Ser Ala Thr Val Ala Leu Gly Cys
                805                 810                 815
Met Phe Val Pro Lys Val Tyr Ile Ile Leu Ala Lys Pro Glu Arg Asn
                820                 825                 830
Val Arg Ser Ala Phe Thr Thr Ser Thr Val Val Arg Met His Val Gly
        835                 840                 845
Asp Gly Lys Ser Ser Ser Ala Ala Ser Arg Ser Ser Ser Leu Val Asn
        850                 855                 860
Leu Trp Lys Arg Arg Gly Ser Ser Gly Glu Thr Leu Arg Tyr Lys Asp
865                 870                 875                 880
Arg Arg Leu Ala Gln His Lys Ser Glu Ile Glu Cys Phe Thr Pro Lys
                885                 890                 895
Gly Ser Met Gly Asn Gly Gly Arg Ala Thr Met Ser Ser Ser Asn Gly
                900                 905                 910
Lys Ser Val Thr Trp Ala Gln Asn Glu Lys Ser Ser Arg Gly Gln His
        915                 920                 925
Leu Trp Gln Arg Leu Ser Ile His Ile Asn Lys Lys Glu Asn Pro Asn
        930                 935                 940
Gln Thr Ala Val Ile Lys Pro Phe Pro Lys Ser Thr Glu Ser Arg Gly
945                 950                 955                 960
Leu Gly Ala Gly Ala Gly Ala Gly Gly Ser Ala Gly Val Gly Ala
                965                 970                 975
Thr Gly Gly Ala Gly Cys Ala Gly Ala Gly Pro Gly Gly Pro Glu Ser
                980                 985                 990
Pro Asp Ala Gly Pro Lys Ala Leu Tyr Asp Val Ala Glu Ala Glu Glu
                995                 1000                1005
His Phe Pro Ala Pro Ala Arg Pro Arg Ser Pro Ser Pro Ile Ser Thr
                1010                1015                1020
```

```
Leu Ser His Arg Ala Gly Ser Ala Ser Arg Thr Asp Asp Val Pro
1025                1030                1035                1040

Ser Leu His Ser Glu Pro Val Ala Arg Ser Ser Ser Gln Gly Ser
                1045                1050                1055

Leu Met Glu Gln Ile Ser Ser Val Val Thr Arg Phe Thr Ala Asn Ile
            1060                1065                1070

Ser Glu Leu Asn Ser Met Met Leu Ser Thr Ala Ala Pro Ser Pro Gly
        1075                1080                1085

Val Gly Ala Pro Leu Cys Ser Ser Tyr Leu Ile Pro Lys Glu Ile Gln
    1090                1095                1100

Leu Pro Thr Thr Met Thr Thr Phe Ala Glu Ile Gln Pro Leu Pro Ala
1105                1110                1115                1120

Ile Glu Val Thr Gly Gly Ala Gln Pro Ala Ala Gly Ala Gln Ala Ala
                1125                1130                1135

Gly Asp Ala Ala Arg Glu Ser Pro Ala Ala Gly Pro Glu Ala Ala Ala
                1140                1145                1150

Ala Lys Pro Asp Leu Glu Glu Leu Val Ala Leu Thr Pro Pro Ser Pro
        1155                1160                1165

Phe Arg Asp Ser Val Asp Ser Gly Ser Thr Thr Pro Asn Ser Pro Val
    1170                1175                1180

Ser Glu Ser Ala Leu Cys Ile Pro Ser Ser Pro Lys Tyr Asp Thr Leu
1185                1190                1195                1200

Ile Ile Arg Asp Tyr Thr Gln Ser Ser Ser Pro Leu
                1205                1210

(2) INFORMATION FOR SEQ ID NO:6:

(i) SEQUENCE CHARACTERISTICS:
        (A) LENGTH: 4303 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:6:

GUGAUACAGA CCAGUGAGAA GGCAGCUUCU CCUUUUCACC UUCUUCUCCA UUCGCUACAU      60

GGGAUUUUAU UGUUCAGAGU UUCUCAGGAC AAAGCUAGAG CUAAUUGUG UCUCUAAUCC      120

UGGGCACUGG CCAUUUGAAG CAGCCAAAGG UGCAUUGACC AGGACUACGU GCAGCCCUUC     180

CUCCAGUGGG ACAUAAGCAG GGGUUUUCUG UGGAAGUCUU AGUUGCAUGA CAUUCUACUG     240

UCAGCUGUGG AGUGUUCAGG UUUAGAAGAU CAUGACCACA UGGAUCAUCU AACUAAAUGG     300

UACAUGGGGA CAAAAUGGUC CUUUAGAAAA UACAUCUGAA UUGCUGGCUA AUUUCUUGAU     360

UUGCGACUCA ACGUAGGACA UCGCUUGUUC GUAGCUAUCA GAACCCUCCU GAAUUCUCCC     420

CACCUUGCUA UCUUUAUUGG CUUGAACUCC UUUCCUAAAA UGGUCCUUCU GUUGAUCCUG     480

UCAGUCUUAC UUUUGAAAGA AGAUGUCCGU GGGAGUGCAC AGUCCAGUGA GAGGAGGGUG     540

GUGGCUCACA UGCCGGGUGA CAUCAUUAUU GGAGCUCUCU UUUCUGUUCA UCACCAGCCU     600

ACUGUGGACA AAGUUCAUGA GAGGAAGUGU GGGGCGGUCC GUGAACAGUA UGGCAUUCAG     660

AGAGUGGAGG CCAUGCUGCA UACCCUGGAA AGGAUCAAUU CAGACCCCAC ACUCUUGCCC     720

AACAUCACAC UGGCUGUGA GAUAAGGGAC UCCUGCUGGC AUUCGGCUGU GGCCCUAGAG      780

CAGAGCAUUG AGUUCAUAAG AGAUUCCCUC AUUUCUUCAG AAGAGGAAGA AGGCUUGGUA     840

CGCUGUGUGG AUGGCUCCUC CUCUUCCUUC CGCUCCAAGA AGCCCAUAGU AGGGGUCAUU     900
```

-continued

```
GGGCCUGGCU CCAGUUCUGU AGCCAUUCAG GUCCAGAAUU UGCUCCAGCU UUUCAACAUA      960

CCUCAGAUUG CUUACUCAGC AACCAGCAUG GAUCUGAGUG ACAAGACUCU GUUCAAAUAU     1020

UUCAUGAGGG UUGUGCCUUC AGAUGCUCAG CAGGCAAGGG CCAUGGUGGA CAUAGUGAAG     1080

AGGUACAACU GGACCUAUGU AUCAGCCGUG CACACAGAAG GCAACUAUGG AGAAAGUGGG     1140

AUGGAAGCCU UCAAAGAUAU GUCAGCGAAG GAAGGGAUUU GCAUCGCCCA CUCUUACAAA     1200

AUCUACAGUA AUGCAGGGGA GCAGAGCUUU GAUAAGCUGC UGAAGAAGCU CACAAGUCAC     1260

UUGCCCAAGG CCCGGGUGGU GGCCUGCUUC UGUGAGGGCA UGACGGUGAG AGGUCUGCUG     1320

AUGGCCAUGA GGCGCCUGGG UCUAGCGGGA GAAUUUCUGC UUCUGGGCAG UGAUGGCUGG     1380

GCUGACAGGU AUGAUGUGAC AGAUGGAUAU CAGCGAGAAG CUGUUGGUGG CAUCACAAUC     1440

AAGCUCCAAU CUCCCGAUGU CAAGUGGUUU GAUGAUUAUU AUCUGAAGCU CCGGCCAGAA     1500

ACAAACCACC GAAACCCUUG GUUCAAGAA UUUGGCAGC AUCGUUUUCA GUGCCGACUG     1560

GAAGGGUUUC CACAGGAGAA CAGCAAAUAC AACAAGACUU GCAAUAGUUC UCUGACUCUG     1620

AAAACACAUC AUGUUCAGGA UUCCAAAAUG GGAUUUGUGA UCAACGCCAU CUAUUCGAUG     1680

GCCUAUGGGC UCCACAACAU GCAGAUGUCC CUCUGCCCAG GCUAUGCAGG ACUCUGUGAU     1740

GCCAUGAAGC CAAUUGAUGG ACGGAAACUU UUGGAGUCCC UGAUGAAAAC CAAUUUUACU     1800

GGGGUUUCUG GAGAUACGAU CCUAUUCGAU GAGAAUGGAG ACUCUCCAGG AAGGUAUGAA     1860

AUAAUGAAUU UCAAGGAAAU GGGAAAAGAU UACUUUGAUU AUAUCAACGU UGGAAGUUGG     1920

GACAAUGGAG AAUUAAAAAU GGAUGAUGAU GAAGUAUGGU CCAAGAAAAG CAACAUCAUC     1980

AGAUCUGUGU GCAGUGAACC AUGUGAGAAA GGCCAGAUCA AGGUGAUCCG AAAGGGAGAA     2040

GUCAGCUGUU GUUGGACCUG UACACCUUGU AAGGAGAAUG AGUAUGUCUU UGAUGAGUAC     2100

ACAUGCAAGG CAUGCCAACU GGGGUCUUGG CCCACUGAUG AUCUCACAGG UUGUGACUUG     2160

AUCCCAGUAC AGUAUCUUCG AUGGGGUGAC CCUGAACCCA UUGCAGCUGU GGUGUUUGCC     2220

UGCCUUGGCC UCCUGGCCAC CCUGUUUGUU ACUGUAGUCU UCAUCAUUUA CCGUGAUACA     2280

CCAGUAGUCA AGUCCUCAAG CAGGGAACUC UGCUACAUUA UCCUUGCUGG CAUCUGCCUG     2340

GGCUACUUAU GUACCUUCUG CCUCAUUGCG AAGCCCAAAC AGAUUUACUG CUACCUUCAG     2400

AGAAUUGGCA UUGGUCUCUC CCCAGCCAUG AGCUACUCAG CCCUUGUAAC AAAGACCAAC     2460

CGUAUUGCAA GGAUCCUGGC UGGCAGCAAG AAGAAGAUCU GUACCAAAAA GCCCAGAUUC     2520

AUGAGUGCCU GUGCCCAGCU AGUGAUUGCU UUCAUUCUCA UAUGCAUCCA GUGGGCAUC     2580

AUCGUUGCCC UCUUUAUAAU GGAGCCUCCU GACAUAAUGC AUGACUACCC AAGCAUUCGA     2640

GAAGCUACC UGAUCUGUAA CACCACCAAC CUAGGAGUUG UCACUCCACU GGAUACAAU     2700

GGAUUGUUGA UUUUGAGCUG CACCUUCUAU GCGUUCAAGA CCAGAAAUGU UCCAGCUAAC     2760

UUCAACGAGG CCAAGUAUAU CGCCUUCACA AUGUACACGA CCUGCAUUAU AUGGCUAGCU     2820

UUUGUGCCAA UCUACUUUGG CAGCAACUAC AAAAUCAUCA CCAUGUGUUU CUCGGUCAGC     2880

CUCAGUGCCA CAGUGGCCCU AGGCUGCAUG UUUGUGCCGA AGGUGUACAU CAUCCUGGCC     2940

AAACCAGAGA GAAACGUGCG CAGCGCCUUC ACCACAUCUA CCGUGGUGCG CAUGCAUGUA     3000

GGGGAUGGCA AGUCAUCCUC CGCAGCCAGC AGAUCCAGCA GCCUAGUCAA CCUGUGGAAG     3060

AGAAGGGGCU CCUCUGGGGA AACCUUAAGG UACAAAGACA GGAGACUGGC CCAGCACAAG     3120

UCGGAAAUAG AGUGUUUCAC CCCCAAAGGG AGUAUGGGGA AUGGUGGGAG AGCAACAAUG     3180

AGCAGUUCCA AUGGAAAAAU CGUCACGUGG GCCCAGAAUG AGAAGAGCAG CCGGGGGCAG     3240
```

-continued

| | | | | |
|---|---|---|---|---|
| CACCUGUGGC | AGCGCCUGUC | CAUCCACAUC | AACAAGAAAG | AAAACCCCAA CCAAACGGCC 3300 |
| GUCAUCAAGC | CCUUCCCCAA | GAGCACGGAG | AGCCGUGGCC | UGGGCGCUGG CGCUGGCGCA 3360 |
| GGCGGGAGCG | CUGGGGGCGU | GGGGGCCACG | GGCGGUGCGG | GCUGCGCAGG CGCCGGCCCA 3420 |
| GGCGGGCCCG | AGUCCCCAGA | CGCCGGCCCC | AAGGCGCUGU | AUGAUGUGGC CGAGGCUGAG 3480 |
| GAGCACUUCC | CGGCGCCCGC | GCGGCCGCGC | UCACCGUCGC | CCAUCAGCAC GCUGAGCCAC 3540 |
| CGCGCGGGCU | CGGCCAGCCG | CACGGACGAC | GAUGUGCCGU | CGCUGCACUC GGAGCCUGUG 3600 |
| GCGCGCAGCA | GCUCCUCGCA | GGGCUCCCUC | AUGGAGCAGA | UCAGCAGUGU GGUCACCCGC 3660 |
| UUCACGGCCA | ACAUCAGCGA | GCUCAACUCC | AUGAUGCUGU | CCACCGCGGC CCCCAGCCCC 3720 |
| GGCGUCGGCG | CCCCGCUCUG | CUCGUCCUAC | CUGAUCCCCA | AAGAGAUCCA GUUGCCCACG 3780 |
| ACCAUGACGA | CCUUUGCCGA | AAUCCAGCCU | CUGCCGGCCA | UCGAAGUCAC GGGCGGCGCG 3840 |
| CAGCCCGCGG | CAGGGGCGCA | GGCGGCUGGG | GACGCGGCCC | GGGAGAGCCC CGCGGCCGGU 3900 |
| CCCGAGGCUG | CGGCCGCCAA | GCCAGACCUG | GAGGAGCUGG | UGGCUCUCAC CCCGCCGUCC 3960 |
| CCCUUCAGAG | ACUCGGUGGA | CUCGGGGAGC | ACAACCCCCA | ACUCGCCAGU GUCCGAGUCG 4020 |
| GCCCUCUGUA | UCCCGUCGUC | UCCCAAAUAU | GACACUCUUA | UCAUAAGAGA UUACACUCAG 4080 |
| AGCUCCUCGC | CGCUGUGAAU | GUCCCUGGAA | AGCACGCCGG | CCUGCGCGUG CGGAGCGGAG 4140 |
| CCCCCCGUGU | UCACACACAC | ACAAUGGCAA | GCAUAGCCGC | CUGGUUACGG CCCAGGGGGA 4200 |
| AGGUGCCAAG | GGCACCCCUU | UAUGGAAACA | CGAGAUCAGU | AGCGCUAUCU CAUGACAACC 4260 |
| CACGAAGAAA | CCGACGACAA | AUCUCGCGGC | AGAUUUUCUU | CUA 4303 |